US010624554B2

(12) United States Patent
Zeidan et al.

(10) Patent No.: US 10,624,554 B2
(45) Date of Patent: Apr. 21, 2020

(54) NON-OVERLAPPING LOOP-TYPE OR SPLINE-TYPE CATHETER TO DETERMINE ACTIVATION SOURCE DIRECTION AND ACTIVATION SOURCE TYPE

(71) Applicant: Biosense Webster (Israel) Ltd., Yokneam (IL)

(72) Inventors: Ziyad Zeidan, Zemmer (IL); Gal Hayam, Tivon (IL)

(73) Assignee: Biosense Webster (Israel) Ltd., Yokneam (IL)

(*) Notice: Subject to any disclaimer, the term of this patent is extended or adjusted under 35 U.S.C. 154(b) by 479 days.

(21) Appl. No.: 15/404,231

(22) Filed: Jan. 12, 2017

(65) Prior Publication Data

US 2017/0202472 A1 Jul. 20, 2017

Related U.S. Application Data

(60) Provisional application No. 62/278,676, filed on Jan. 14, 2016.

(51) Int. Cl.

*A61B 5/042* (2006.01)
*A61B 5/00* (2006.01)
(Continued)

(52) U.S. Cl.

CPC ............ *A61B 5/0422* (2013.01); *A61B 5/046* (2013.01); *A61B 5/6856* (2013.01); (Continued)

(58) Field of Classification Search

CPC ..... A61B 5/0422; A61B 5/046; A61B 5/6856; A61B 5/6857; A61B 5/6858; A61B 5/6859; A61B 18/1492

See application file for complete search history.

(56) References Cited

U.S. PATENT DOCUMENTS 5,680,860 A * 10/1997 Imran ................ A61B 18/1492 600/374
5,938,694 A * 8/1999 Jaraczewski ......... A61B 5/0422 600/373

(Continued)

FOREIGN PATENT DOCUMENTS

| | | | |
|---|---|---|---|
| CN | 101156774 | A | 4/2008 |
| EP | 2 984 986 | A2 | 2/2016 |
| WO | 2017/024107 | A1 | 2/2017 |

OTHER PUBLICATIONS

Allessie et al., "Electropathological substrate of long-standing persistent atrial fibrillation in patients with structural heart disease: Longitudinal Dissociation," Circulation—Arrhythmia and Electrophysiology, pp. 606-615 (Dec. 2010).

(Continued)

*Primary Examiner* — Linda C Dvorak
*Assistant Examiner* — James A Cipriano

(57) ABSTRACT

A catheter may be adapted to map a chamber of the heart. The catheter may include a magnetic and/or ultrasound sensor for navigation. The body of the catheter may be pliable and configured to form a predetermined shape upon exiting a catheter sheath. Upon exiting the catheter sheath, the catheter body may be configured to form one or more loops, and the loops may be non-overlapping loops. In some examples, the non-overlapping loops may be concentric loops. Alternatively, the catheter body may be configured to form one or more splines. The catheter body may include an embedded electrode assembly. The electrodes of the electrode assembly may be may be arranged in one or more rows and configured to detect a wave front. The electrode assembly may also be configured to generate and activation sequence and determine a direction of an activation source. The electrode assembly may also be configured to determine the type of activation source, for example a rotational (Continued)

activation source, a focal activation source, and a single-wide activation source.

8 Claims, 17 Drawing Sheets

(51) Int. Cl.
*A61B 5/046* (2006.01)
*A61B 18/00* (2006.01)

(52) U.S. Cl.
CPC .......... *A61B 5/6857* (2013.01); *A61B 5/6858* (2013.01); *A61B 5/6859* (2013.01); *A61B 2018/00577* (2013.01)

(56) References Cited

U.S. PATENT DOCUMENTS 6,973,339 B2 12/2005 Govari
8,433,398 B2 4/2013 Zhang
2002/0022839 A1 2/2002 Stewart et al.
2002/0055674 A1 5/2002 Ben-Haim et al.
2003/0093004 A1 5/2003 Sosa et al.
2004/0059237 A1 3/2004 Narayan et al.
2004/0243012 A1 12/2004 Ciaccio et al.
2005/0038333 A1 2/2005 Sra
2007/0197929 A1 8/2007 Porath et al.
2008/0188765 A1 8/2008 Stolarski et al.
2009/0112199 A1 4/2009 Zhang et al.
2009/0253974 A1 10/2009 Rahme
2009/0299447 A1* 12/2009 Jensen ................. A61N 1/0587 607/130
2011/0054560 A1 3/2011 Rosenberg et al.
2011/0125041 A1 5/2011 Fischell et al.
2011/0230775 A1 9/2011 Barley et al.
2011/0251505 A1 10/2011 Narayan et al.
2013/0006131 A1 1/2013 Narayan et al.
2013/0116681 A1 5/2013 Zhang
2013/0131746 A1 5/2013 Simon et al.
2013/0274582 A1 10/2013 Afonso et al.
2014/0005563 A1 1/2014 Ramanathan et al.
2014/0052118 A1* 2/2014 Laske ................. A61B 5/6852 606/32
2014/0081114 A1 3/2014 Shachar et al.
2014/0336520 A1 11/2014 Zeng et al.
2015/0216435 A1 8/2015 Bokan et al.
2015/0216438 A1 8/2015 Bokan et al.
2016/0045123 A1 2/2016 Bar-Tal et al.

OTHER PUBLICATIONS

De Groot et al., "Electropathological Substrate of Longstanding Persistent Atrial Fibrillation in Patients With Structural Heart Disease: Epicardial Breakthrough," Circulation, pp. 1674-1682 (Oct. 26, 2010).
Houben et al., "S-wave predominance of epicardial electrograms during atrial fibrillation in humans: Indirect evidence for a role of the thin subepicardial layer," Heart Rhythm, vol. 1, No. 6, pp. 639-647 (Dec. 2004).
Inoue et al., "Trigger-based mechanism of the persistence of atrial fibrillation and its impact on the efficacy of catheter ablation," Circulation—Arrhythmia and Electrophysiology, pp. 295-301 (Apr. 2012).
Lee et al., "Simultaneous Bi-Atrial High Density (510-512 Electrodes) Epicardial Mapping of Persistent and Long-Standing Persistent Atrial Fibrillation in Patients: New Insights into the Mechanism of Its Maintenance," Circulation, vol. 132, Issue 22, pp. 2108-2117 (Dec. 1, 2015).
Lee et al., "Simultaneous Bi-Atrial High Density (510-512 Electrodes) Epicardial Mapping of Persistent and Long-Standing Persisten Atrial Fibrillation in Patients: New Insights into the Mechanism of Its Maintenance," Circulation, vol. 132, Issue 22, pp. 2108-2117 (Dec. 1, 2015).
Narayan, et al. "Classifying Fractionated Electrograms in Human Atrial Fibrillation Using Monophasic Action Potentials and Activation Mapping: Evidence for Localized Drivers, Rate Acceleration, and Nonlocal Signal Etiologies," Heart Rhythm, Elsevier, US, vol. 8, No. 2, Oct. 11, 2010, pp. 244-253.
Houben, et al. "S-Wave Predominance of Epicardial Electrograms During Atrial Fibrillation in Humans: Indirect Evidence for a Role of the Thin Subepicardial Layer," Heart Rhythm, Elsevier, US, vol. 1, No. 6, Dec. 1, 2004, pp. 639-647.
Communication Pursuant to Article 94(3) EPC dated Aug. 28, 2018 for the European Patent Application No. 17151634.7.
Communication Pursuant to Article 94(3) EPC dated Aug. 28, 2018 for the European Patent Application No. 17151625.5.
Extended European Search Report dated May 18, 2017 for the European Patent Application No. 17151625.5.
Extended European Search Report dated May 26, 2017 for the European Patent Application No. 17151629.7.

* cited by examiner

NON-OVERLAPPING LOOP-TYPE OR SPLINE-TYPE CATHETER TO DETERMINE ACTIVATION SOURCE DIRECTION AND ACTIVATION SOURCE TYPE

CROSS REFERENCE TO RELATED APPLICATION

This application claims the benefit of U.S. Provisional Application No. 62/278,676 filed on Jan. 14, 2016, which is incorporated by reference as if fully set forth. This application incorporates by reference as if fully set forth U.S. patent application Ser. No. 15/404,228 titled "Region of Interest Focal Source Detection Using Comparisons of R-S Wave Magnitudes and LATs of RS Complexes," U.S. patent application Ser. No. 15/404,225 titled "Region of Interest Rotational Activity Pattern Detection," U.S. patent application Ser. No. 15/404,244 titled "Identification of Fractionated Signals," U.S. patent application Ser. No. 15/404,226 titled "Overall System and Method for Detecting Regions of Interest," and U.S. patent application Ser. No. 15/404,266 titled "Region of Interest Focal Source Detection," all filed on Jan. 12, 2017.

SUMMARY

A catheter may be adapted to map a chamber of the heart. The catheter may include a magnetic and/or ultrasound sensor for navigation. The body of the catheter may be pliable and configured to form a predetermined shape upon exiting a catheter sheath. Upon exiting the catheter sheath, the catheter body may be configured to form one or more loops, and the loops may be non-overlapping loops. In some examples, the non-overlapping loops may be concentric loops. Alternatively, the catheter body may be configured to form one or more splines.

The catheter body may include an embedded electrode assembly. The electrode assembly may be configured to detect a wave front. The electrode assembly may also be configured to generate an activation sequence and determine a direction of an activation source. The electrode assembly may also be configured to determine the type of activation source, for example a rotational activation source, a focal activation source, and a single-wide activation source. The arrangement and density of the electrodes on the catheter may enable the precise location of an activation source, for example a focal activation source and determination of a re-entry pathway.

The electrode assembly may include two or more electrodes. The electrodes may be arranged in one or more rows. Each row of electrodes may be formed by one or more non-overlapping loops. The electrodes in each row may be arranged such that they are in direct alignment. In an example where the catheter is configured with four rows of electrodes, each row of electrodes may be arranged such that it is separated from the next row of electrodes by 90 degrees. In an example where the catheter is configured with less than four rows of electrodes, each row of electrodes may be arranged such that it is separated from the next row of electrodes by more than 90 degrees. Conversely, in an example where the catheter is configured with more than four rows of electrodes, each row of electrodes may be arranged such that it is separated from the next row of electrodes by less than 90 degrees.

In an example where the catheter body is configured to form one or more splines, the electrode assembly may include two or more electrodes. The electrodes may be arranged in one or more rows. Each row of electrodes may be formed on each spline. The electrodes in each row may be arranged such that they are in direct alignment. In an example where the catheter is configured with four splines resulting in four rows of electrodes, each spline may be arranged such that it is separated from the next spline by 90 degrees. In an example where the catheter is configured with less than four splines, each spline may be arranged such that it is separated from the next spline by more than 90 degrees. Conversely, in an example where the catheter is configured with more than four splines, each spline may be arranged such that it is separated from the next spline by less than 90 degrees.

A system and method may be used to display an optimal configuration based on a sequence of activation along each row of electrodes of the catheter. This example system and method may measure local activation times (LAT)s and use the LATs to determine the direction and/or propagation of a wave front. The system and method may also use the LATs to determine the type of activation source. The system may indicate and display the catheter electrodes with the earliest activation and the wave front propagation on an anatomical map.

A method of mapping may be based on the concept of identifying the activation sequence at any point or location and tracing the origin of the activation. The signals recorded by the catheter may be arranged in a specific configuration to enable the identification of the wave front direction of activation and determine the origin.

The system may use the method to indicate a direction of the activation origin to direct the user to move the catheter to a new location. At the new location, the system may again determine the direction of the activation origin to further direct the user to move the catheter towards the activation origin. The activation of origin may be identified based on predefined activation patterns. The system may alert the user upon reaching the origin of activation. The determination of the location and identifying the mechanism of activation origins and triggers may be performed automatically by the system. The user may confirm by visually reviewing the sequence of recorded signals at the location.

BRIEF DESCRIPTION OF THE DRAWINGS

A more detailed understanding can be had from the following description, given by way of example in conjunction with the accompanying drawings wherein.

DETAILED DESCRIPTION OF THE EMBODIMENTS

Figure 1:
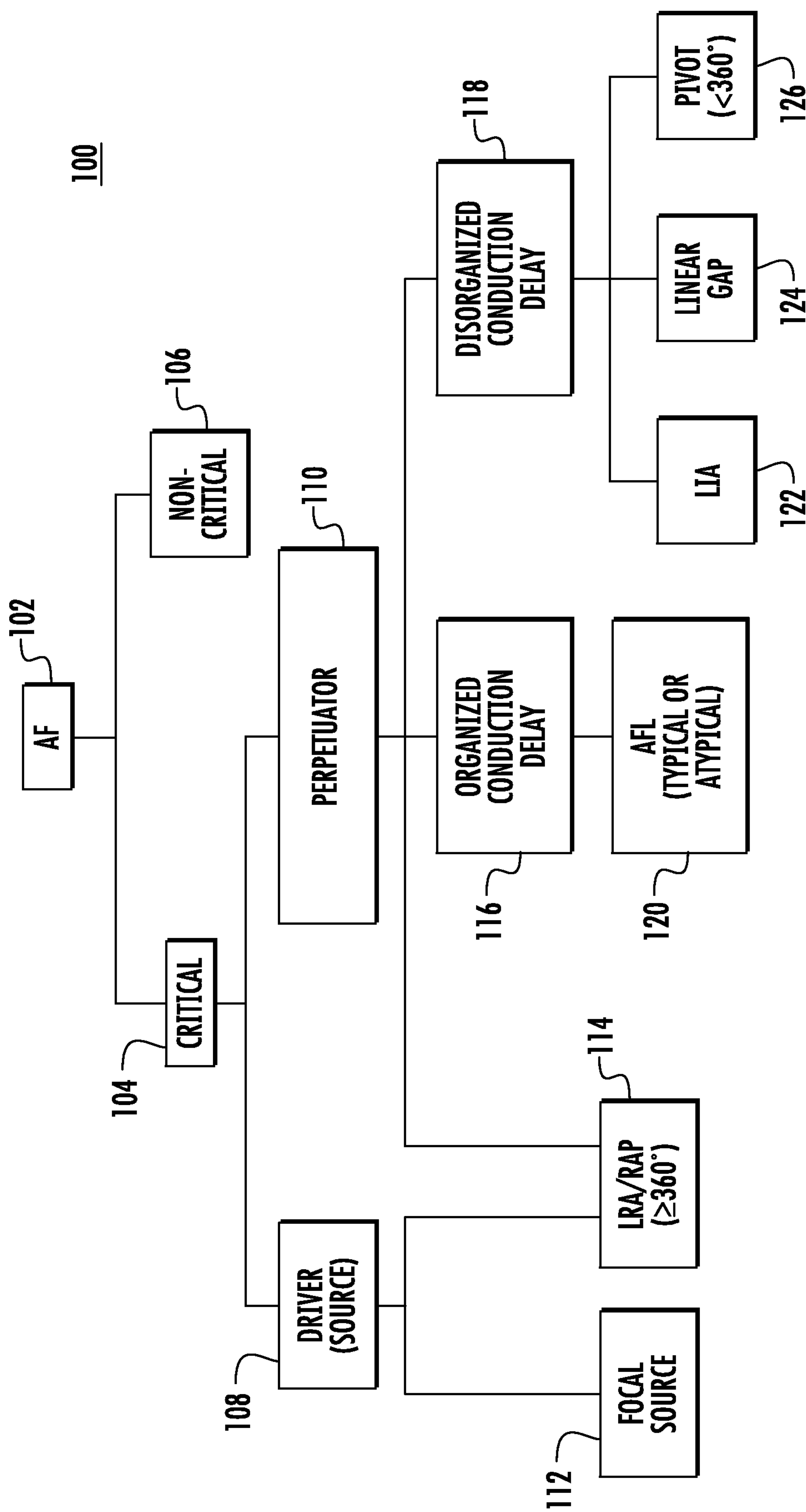
FIG. 1 is a block diagram illustrating an exemplary hierarchical classification of AF used with embodiments disclosed herein.

Cardiac arrhythmia includes different types of abnormal or irregular heart rhythms, such as, for example, atrial fibrillation (AF), which is characterized by rapid and irregular beating. In patients with normal sinus rhythm, the heart, which is comprised of atrial, ventricular, and excitatory conduction tissue is electrically excited to beat in a synchronous, patterned fashion. In patients with cardiac arrhythmias, abnormal regions of cardiac tissue do not follow the synchronous beating cycle associated with normal sinus rhythm. Instead, the abnormal regions of cardiac tissue aberrantly conduct to the adjacent tissue, thereby disrupting the cardiac cycle into an asynchronous cardiac rhythm. Such abnormal conduction has been previously known to occur at various regions of the heart, such as, for example, in the region of the sino-atrial (SA) node, along the conduction pathways of the atrioventricular (AV) node and the Bundle of His, or in the cardiac muscle tissue forming the walls of the ventricular and atrial cardiac chambers.

Cardiac arrhythmias, including atrial arrhythmias, may be of a multiwavelet re-entrant type, characterized by multiple asynchronous loops of electrical impulses that are scattered about the atrial chamber and are often self propagating. Alternatively, or in addition to the multiwavelet re-entrant type, cardiac arrhythmias may also have a focal origin, such as when an isolated region of tissue in an atrium fires autonomously in a rapid, repetitive fashion or a rotational activity pattern (RAP), such as where an irregular region of the heart expresses rotating electrical pulses.

The mapping and treatment of AF, particularly persistent AF, are a significant challenge. The conventional treatment of AF using radio frequency (RF) energy consists of creating an ablation line surrounding the antrum of the pulmonary vein (PV) in order to isolate any ectopic electrical activity and prevent the ectopic electrical activity from propagating to the atrium. Additional ablation lines and/or substrate modulation usually are added to conventional pulmonary vein isolation (PVI) treatments. This treatment revealed unsatisfactory long term results. For example, almost 50% of the treated patients experience recurrence of atrial fibrillation within 1-2 years following the procedure. In addition, the conventional mapping methods of cardiac activation are not suitable for the mapping of AF, as the mechanism of AF is not well defined. In addition to the ectopic beats that are originated at the PVs and trigger AF, other mechanisms in regions other than the PV play a significant role in the initiation and maintaining of AF. Accordingly, PVI has thus far achieved unsatisfactory long term outcomes in the treatment of AF.

Electrophysiologists are therefore searching for additional triggers that originate from regions other than the PV as potential mechanisms for AF to target with RF ablation. Various approaches and technologies have been developed in order to explore and locate these triggers. The most recognized technologies are based on global mapping of the atria using endocardial mapping with a basket type catheter or extra-cardiac mapping, with specific algorithms for the generation of activation maps.

Each of these existing technologies has shown the capability of determining additional triggers originating out of the PVs in the form of re-entrant activity or focal triggers. All of these existing technologies, however, share some basic limitations of low resolution and area of coverage of the mapped chamber. In addition, there are specific limitations relating to the uncertainty of findings as a result of the processing methods in each technology.

Conventional methods and systems used for catheter ablation typically include inserting the catheter through an incision in the skin and guided up to the heart. Before ablation is performed, intra-cardiac electrocardiogram (IC ECG) signals of the heart are acquired via electrodes placed at different areas of the heart. The signals are monitored and used to provide information to determine whether one or more areas of the heart are causing the irregular heart rhythm. The conventional methods and systems used to determine these areas to be ablated, however, are time consuming (e.g., hours) and rely on medical personnel with specific expertise and experience requiring many hours of training. It would therefore be desirable that a catheter is adapted to more easily map a chamber of the heart based on the concept of identifying the activation sequence at any anatomical point to trace the origin of the activation.

Embodiments disclosed herein employ systems, apparatuses and methods of determining potential regions of interest (ROIs) to be targeted for ablation. Various mapping techniques are utilized to provide maps of the electrophysical conditions of the AF substrate and maps representing a spatio-temporal manifestation of the AF process to provide efficient and accurate determination of potential ablation ROIs. Mapping techniques utilize various parameters (e.g., cycle, earliness, R-S complex, conduction velocity (CV), block and fractionation) of acquired IC ECG signals and detected LATs to identify potential evidence of drivers and perpetuators of the AF substrate. Identification of the potential evidence of drivers and perpetuators is used to provide mapping (e.g., driver maps and perpetuator maps)

of the AF substrate. Mapping techniques also include utilizing the various parameters of the acquired IC ECG signals and detected local activation times to provide mapping (e.g., activation/wave maps, CV maps, fractionation maps, voltage maps and block maps) which potentially represents the spatio-temporal manifestation of the AF process. The mapping of the spatio-temporal manifestation of the AF process can be used in addition to or alternative to, the mapping of the AF substrate to identify potential ablation ROIs. The mapping techniques are used to potentially reduce AF map analysis training time, increase success rates resulting from ablation and facilitate efficient interpretation of AF maps. For simplification purposes, embodiments described herein refer to systems and methods used for the treatment of AF. It is noted however, embodiments may be used for the treatment of any type of cardiac arrhythmia including different types of abnormal or irregular heart rhythms.

FIG. 1 is a block diagram illustrating an exemplary classification of AF used with embodiments disclosed herein. The exemplary classification in FIG. 1 distinguishes between critical and non-critical AF as well as between drivers and perpetuators of AF and their relative spatio-temporal patterns.

For example, as shown in FIG. 1, an irregular heart rhythm characterized as AF 102 is classified as critical 104 or non-critical 106. Examples of non-critical AF 106 includes paroxysmal (i.e., intermittent) irregular heart rhythm episodes in which the heartbeat often normalizes as quickly as within a few seconds or after a few hours, and persistent irregular heart rhythm episodes in which a normal heart may be restored by rhythm medical therapy or a procedure (e.g., cardioversion). Examples of critical AF 104 include longstanding persistent irregular heart rhythm episodes that continue for longer periods of time (e.g., more than a year) in which the heart is in a constant state of AF and the condition is considered permanent.

Critical AF can be classified according to characteristics (e.g., areas of activation) that can be derived from IC ECG signals. Areas of activation may be identified as potential contributing factors to AF. As shown in FIG. 1, critical AF is classified according to different areas of activation, including a potential driver of AF (hereinafter driver) or potential source of AF (hereinafter source) 108 and a potential perpetuator 110 of AF (hereinafter perpetuator). A driver 108 is an area of activation (e.g., in the atria) where electrical pulses originate to stimulate the heart to contract and which can potentially contribute to AF, for example, by producing fibrillatory conduction to other areas of the atria. A perpetuator 110 is an area of sustained activation (e.g., electrophysiological process/substrate) which can also potentially contribute to AF.

Drivers 108 and perpetuators 110 may be represented (e.g., mapped) according to their spatio-temporal manifestation. As shown in FIG. 1, drivers 108 and perpetuators 110 are classified by exemplary spatio-temporal manifestation types, including focal sources (foci) 112 and localized rotational activation (LRA) sources or rotational activation patterns (RAPs) sources 114. A focal source is a type of driver originating at a small area of the atria which spreads centrifugally from a single point. A RAP 114 source is a region of the heart where the electrical pulses rotate at least 360 degrees about a center area.

FIG. 1 also shows different types of perpetuators 110, including one type which exhibits organized conduction delay 116 and another which exhibits disorganized conduction delay 118. Another type of perpetuator 110 shown in FIG. 1 includes atrial flutter (AFL) 120 characterized by organized conduction delay 116 as well as localized irregular activation (LIA) 122, linear gaps 124 and pivots 126 (i.e., electrical pulses that rotate less than 360 degrees about a center area) exhibiting behavior characterized by disorganized conduction delay 118. Also, the RAP source 114 is shown as both a driver type and a perpetuator type. Drivers 108 and perpetuators 110 are, for example, separately mapped to facilitate identification of types of drivers 108 and/or types of perpetuators 110 and provide efficient and accurate determination of potential ablation ROIs.

Mapping and identification of drivers 108 and perpetuators 110 may also be based on one or more additional factors which may potentially contribute to AF or parameters which may potentially characterize the AF substrate (i.e., the AF process itself) and/or the manifestation of the AF process. For example, AF parameters or AF factors used to identify potential focal sources 108 include omnidirectional activation spread of activation from a point, earliness (e.g., focal source which starts after an excitable gap), triggers such as fast firing (e.g., short cycle-length and high dominant frequency) foci and breakthroughs (e.g., PV, free wall and transmural, endocardial and epicardial) and micro re-entry circuit which manifests as focal source and short-radius re-entry circuits which can manifest as a driver 108 depending on the specific anisotropic structure of the central obstacle.

AF parameters or AF factors used to map and identify RAP sources 114 include, for example, repetitive cycles, rotors which can manifest as a driver source 108, structural or functional anisotropy (e.g., localized or distributed), and short-radius re-entry circuits which can manifest as either a driver 108 or a perpetuator 110, depending on specific anisotropic structure of the central obstacle.

AF parameters or AF factors used to map and identify perpetuators 110 include, for example, extension (increased) path length, anatomical (pathological) block lines, fibrosis, stable functional block lines (e.g., areas of prolonged refractoriness, criticality (e.g., shortest path around block line>path length) and fibrillatory conduction factors (e.g., dissociated waves, re-entry circuit factors).

Figure 2:
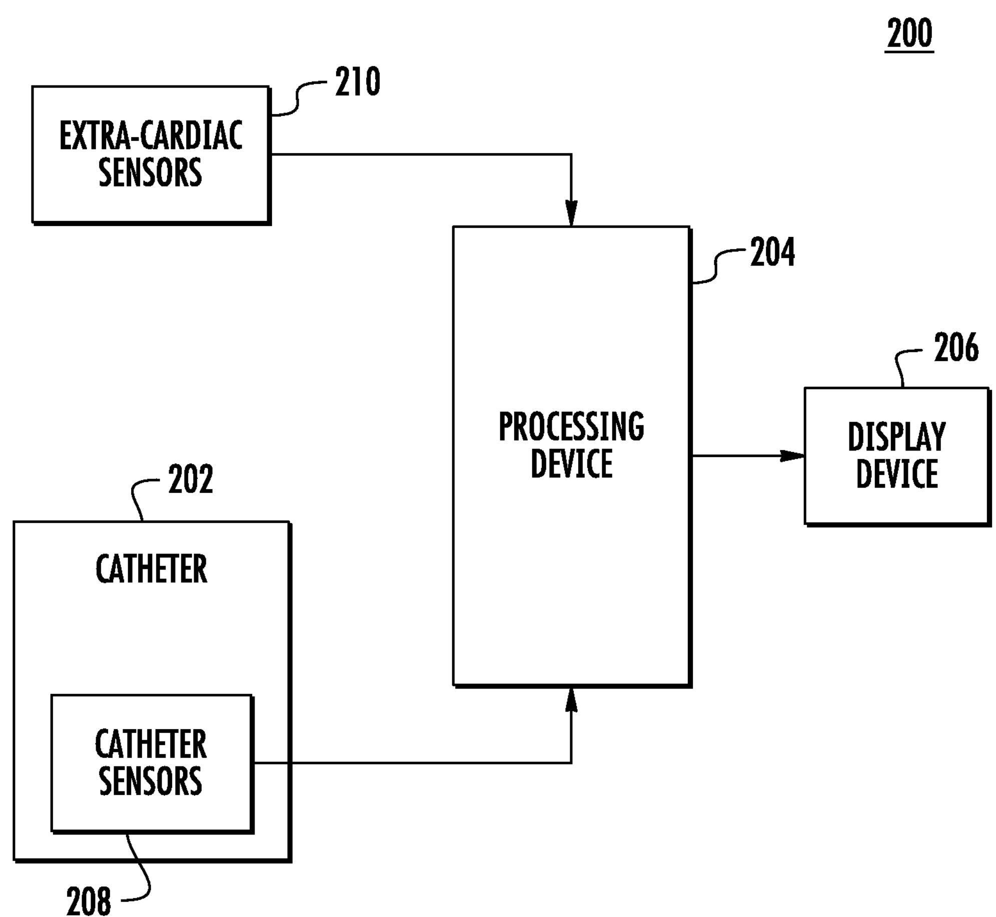
FIG. 2 is a block diagram illustrating an exemplary system used to determine AF ROIs for ablation for use with embodiments disclosed herein.

FIG. 2 is a block diagram illustrating an exemplary system 200 used to determine AF ROIs for ablation for use with embodiments disclosed herein. As shown in FIG. 2, the system 200 includes a catheter 202, a processing device 204 and a display device 206. Catheter 202 includes an array of catheter sensors (e.g., electrodes) each configured to detect electrical activity (electrical signals) of an area of the heart over time. When an IC ECG is performed, each electrode detects the electrical activity of an area of the heart in contact with the electrode. The system 200 also includes extra-cardiac sensors 210 (e.g., electrodes on the skin of a patient) configured to detect electrical activity of the heart via detection of electrical changes on the skin due to the electro-physiologic pattern of the heart.

The detected IC ECG signals and the detected extra-cardiac signals are processed (e.g., recorded over time, filtered, fractionated, mapped, combined, interpolated, etc.) by processing device 204 and displayed on display device 206.

Embodiments include any number of sensors to detect ECG signals, including sensors to detect IC ECG signals and extra-cardiac ECG signals. In some embodiments, disclosed methods of determining ablation ROIs use IC ECG signals and extra-cardiac ECG signals. In some embodiments, methods of determining ablation ROIs use either IC ECG signals or extra-cardiac ECG signals. For example, some methods of determining ablation ROIs use IC ECG signals without using extra-cardiac ECG signals. For simplification purposes, the following examples refer to IC ECG signals, although it is understood that these examples may also apply to, or in combination with, extra-cardiac ECG signals.

Processing device 204 may include one or more processors each configured to process the IC ECG signals. Each processor of processing device 204 may be configured to record IC ECG signals over time, filter ECG signals, fractionate IC ECG signals into signal components (e.g., slopes, waves, complexes), map IC ECG signals, combine IC ECG signal information, map and interpolate mapping information, etc.

Display device 206 may include one or more displays each configured to display ECG signals, ECG signal information, maps of the AF process and maps representing a spatio-temporal manifestation of the AF process.

The catheter sensors 208 and the extra cardiac sensors 210 may be in wired or wireless communication with processing device 204. Display device 206 may also be in wired or wireless communication with processing device 204.

Figure 3A:
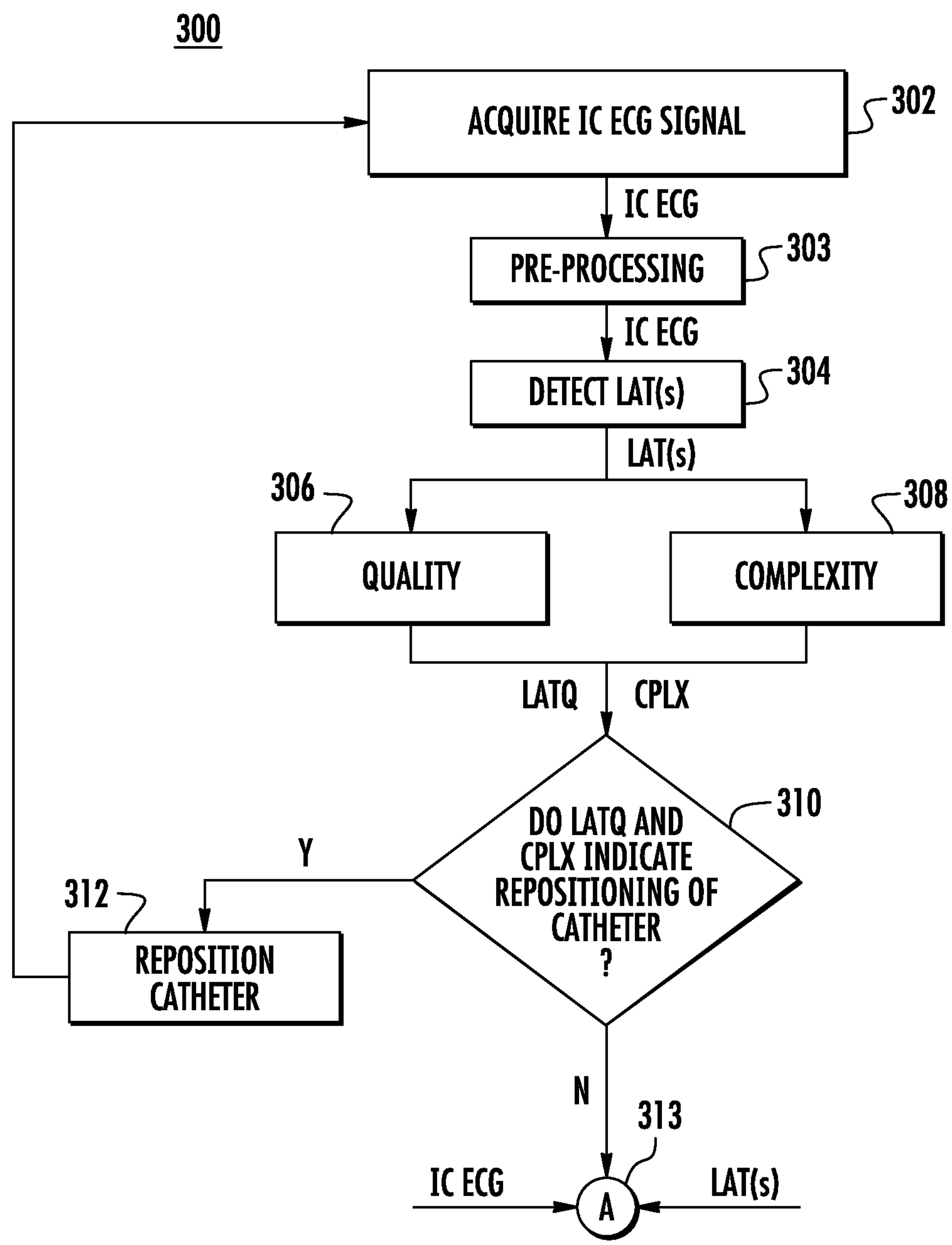
FIGS. 3A and 3B are portions of a flow diagram illustrating an exemplary method of determining an AF ROI for ablation according to an embodiment.
Figure 3B:
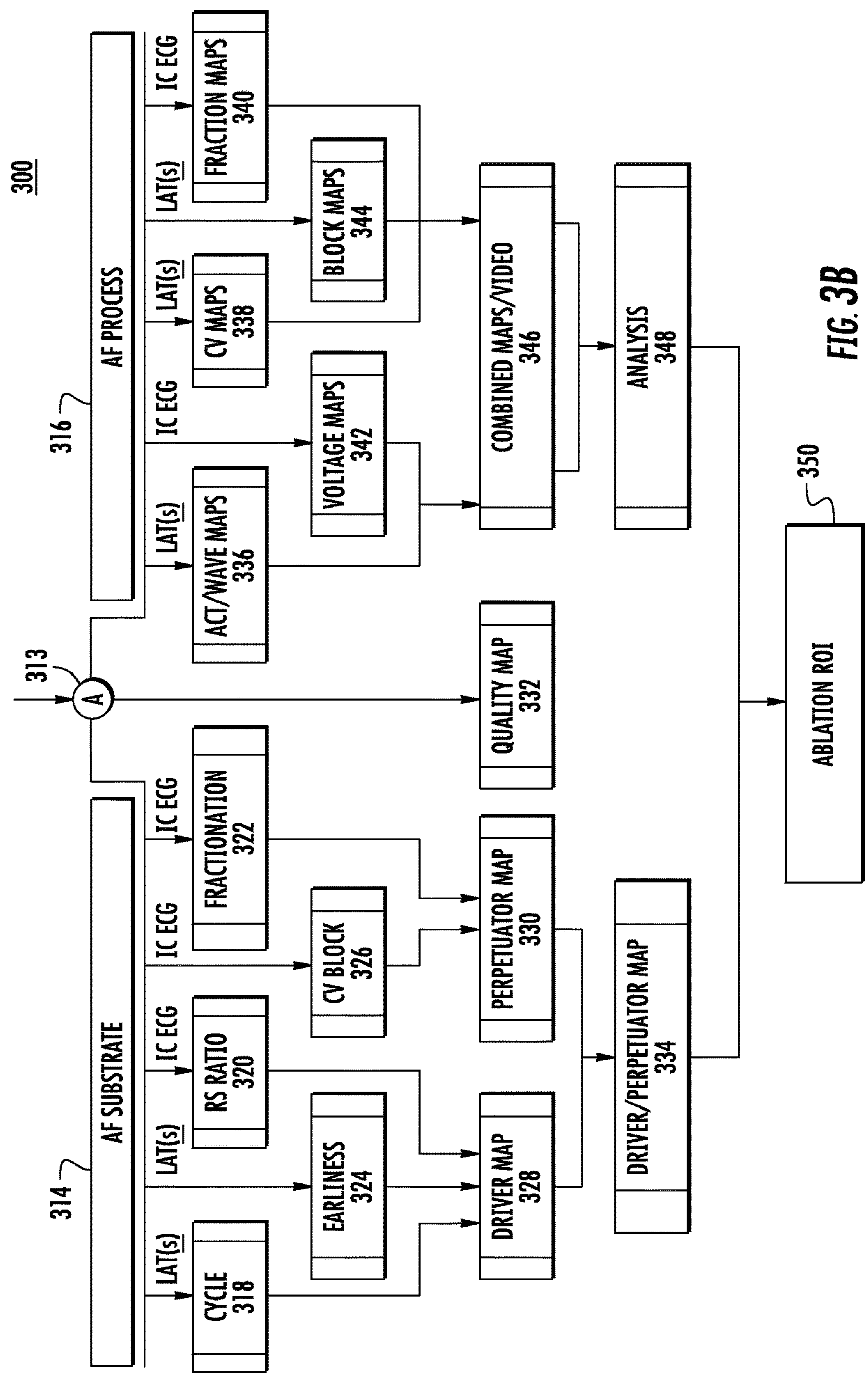

FIGS. 3A and 3B are portions of a flow diagram illustrating an exemplary method 300 of determining an AF ROI. The method 300 employs a mapping taxonomy which includes, from its core moving outward, an IC ECG layer, a pre-processing layer, a LAT detection layer, a map segmentation layer, a map interpolation layer and a map interpretation layer.

FIG. 3A illustrates a portion of exemplary method 300. As shown in block 302 of FIG. 3A, the method 300 includes, as part of the IC ECG layer, acquiring an IC ECG signal which represents electrical activity of an area of the heart. The IC ECG signal acquired at block 302 is, for example, acquired from one of a number of electrodes in contact with different areas of the heart. After acquisition of the IC ECG (302), the method 300 includes, as part of the pre-processing layer, pre-processing of the acquired ECG signal, as shown in block 302 of FIG. 3A, The pre-processing may include execution of one or more algorithms, such as for example, cancellation of ventricular far field signals, baseline correction, and noise reduction. Ventricular far field detection may include, for example, a spatial averaging method (SAM), a temporal averaging method (TAM), a system identification method (SIM) and principal component analysis (PCA).

For each acquired IC ECG signal acquired at block 302, one or more LATs of the corresponding pre-processed IC ECG signal are detected at block 304. The LAT quality (shown as LATQ in FIG. 3A) of each signal is determined at block 306 as part of an exemplary LAT detection layer. The AF complexity (shown as CPLX in FIG. 3A) of the signal is determined at block 308.

As shown at decision point 310, the method 300 includes determining whether to reposition the catheter based on the LAT quality of the signal and the AF complexity. A typical characteristic of high quality IC ECGs include little base line wander (e.g., low baseline vs. IC-ECG RMS amplitude, limited ventricular far-field potentials vs. IC-ECG RMS amplitude). IC-ECG signals characteristics include discernable atrial complexes (e.g., confined (~50 ms) complexes separated by isoelectric segments repeating slopes, (50-200 ms interval; about 150 ms median) during AF. High quality complexes characteristic typically have considerable amplitudes and steep downward slopes (vs. upward slopes) within complexes. Characteristics of the IC ECG signals may be combined into a single measurable characteristic or parameter (e.g., having a measurable value of 0%-100%) to define LAT quality. The LAT quality may be compared to the AF complexity to determine whether to reposition the catheter.

In some embodiments, quality is defined by an ability to map AF for a level of AF complexity. Determining whether to reposition the catheter may include generating a map and determining whether the generated map can be used (e.g., is adequate) to map AF based on whether a level of coverage of a mapping electrode meets (e.g., matches) a level of AF complexity. The ability to map AF for a level of AF complexity may include meeting a map threshold level (e.g., adequate level, trustworthy level). A single parameter (i.e., mapping coverage) is used to define a level of coverage of the mapping electrode. Examples of characteristics that are combined to define the mapping coverage include: (1) contact of the mapping electrode (e.g., contact with active tissue (wall) related to covered area and LAT accuracy); (2) resolution of the electrodes (e.g., distances and electrode sensitivity radii between electrodes, including mean, minimum and maximum and distances); and (3) quality of the IC ECG and associated annotations provided by a detection algorithm.

AF complexity may include complexity of activation during AF creating wave dissociation (block lines), fusion and wave curvature. Accordingly, a map may be determined as a map which can be used (e.g., trustworthy or adequate) to map AF when, given a certain level of AF complexity (e.g., measured along y-axis), the mapping coverage (including signal and annotation quality measured along x-axis) is sufficient to map the AF complexity. If not, the trustworthiness of the map may become compromised or inadequate.

Signals may then be analyzed using the trustworthy or adequate maps to determine whether the catheter should be repositioned. If it is determined at decision point 310 to reposition the catheter, the catheter (e.g., catheter 202) is repositioned at block 312 and a new IC ECG signal is acquired at block 302. If it is determined at decision point 310 that the catheter should be repositioned, the method 300 continues to "point A" 313 (shown in FIG. 3A and FIG. 3B).

FIG. 3A illustrates the acquiring of a single IC ECG signal for simplification purposes. In practice, however, multiple signals are acquired for each of the plurality of electrodes contacting the heart. Each IC ECG signal acquired at block 202 and the one or more LATs detected for each signal at block 204 are received at "point A" 313.

FIG. 3B illustrates exemplary methods which may be used to determine potential ablation ROIs. As shown FIG. 3B, each acquired IC ECG signal and the one or more detected LATs for each signal are used to generate maps of the AF process that includes the electro-physical conditions of the AF substrate (indicated as the AF Substrate 314 in FIG. 3B) and maps representing a spatio-temporal manifestation of the AF process (indicated as the AF Process 316 in FIG. 3B) as part of an exemplary map segmentation layer.

For example, with regard to the AF Substrate 314 shown in FIG. 3B, the one or more detected LATs are used to independently determine one or more factors or parameters which may contribute to AF. The left side of FIG. 3B illustrates methods which characterize the AF substrate by collecting information over a predefined window of time while assessing a mean interval (e.g., cycle) based on a difference of subsequent LATs 318, first activated (earliness) 324, and morphological aspects of the IC ECG including RS-ratio 320 and fractionation 322 (e.g., fractionated electrograms). For example, the detected LATs are used to independently determine cycle information (e.g., cycle lengths) at block 318 and earliness information (e.g., earliest activation times, early drivers which start after an excitable gap) at block 324. Each IC ECG signal is also used to independently determine R-S complex information (e.g., ratio of R wave to S wave) at block 320 and information obtained by fractionation (e.g., slope information, information indicating an incidence of source behavior presented as the earliest activation from one of a plurality of electrodes, such as showing a percentage that the associated electrode was activated earlier than neighbouring electrodes) of the IC ECG signals at block 322 and CV Block information (e.g., information indicating slowed or blocked conduction (i.e., progression) of electrical impulses through the heart, such as the conduction time (CT) for the electrical pulse to travel a distance in the heart, the path length (i.e., the distance) and the CV of the electrical pulse) at block 326.

A driver map 328 is generated from the cycle information 318, the earliness information 324 and the R-S complex information 320. A perpetuator map 330 is generated from the CV Block information 326 and the fractionation information 322. As shown at block 330, the information used to generate the driver map and the information used to generate the perpetuator map are combined (e.g., a single map, overlaid maps or adjacent maps in one display area) to generate a combined driver/perpetuator map 334. The combined driver/perpetuator map 334 may then be used (e.g., interpolated as part of an exemplary map interpolation layer) to determine one or more ablation ROIs at block 350.

With regard to the AF Process 316 shown in FIG. 3B, the one or more detected LATs are used to independently generate activation/wave maps 336, CV maps 338 (e.g., maps generated from the CT, the path length and/or the CV of the electrical pulse) and Block maps 344 (e.g., maps generated from information indicating a block in the conduction of the signal).

Activation/wave maps 336 may, for example, include a map representing an incidence of source behavior presenting the earliest activation of one of a plurality of electrodes restricted by the same wave, such as indicating a percentage of activation waves detected by a corresponding electrode activated earlier than neighboring electrodes though restricted by neighbors activated by the same wave. Activation/wave maps 336 may, for example, also include a map representing the incidence of electrode positions associated with a fibrillation wave start.

Each IC ECG signal is used to independently generate Voltage maps 342 and Fraction Maps 340. The information used to generate maps 336-344 is combined to provide combined maps or video 346. In some embodiments, the information used to generate the Activation/Wave maps 336 and Voltage maps 342 is combined to generate a combined Activation/Wave/Voltage map or video and the information used to generate the CV maps 338, the Block maps 344 and the Fraction maps 340 is combined to generate a combined CV/Block/Fraction map or video. The combined maps/video 346 are analyzed (e.g., interpreted by medical personnel as part of an exemplary map interpretation layer) at block 348 to determine ROIs to be ablated at block 350. The combined maps/video 346 represent a spatio-temporal manifestation of the AF process 316 which can be easily visualized and interpreted, facilitating an efficient and accurate process for determination of ROIs for ablation. Determined ROIs may be represented (e.g., displayed), for example, by color, by 3-D contour on a 4-D map, by icons (e.g., dynamically changing icons), etc.

In some embodiments, both the combined Driver/Perpetuator Map 334 and the combined maps/video 346 are used to determine ROIs for ablation at block 350. In some embodiments either the combined Driver/Perpetuator Map 334 or the combined maps/video 346 are used to determine ROIs for ablation at block 350. For example, the combined Driver/Perpetuator Map 334 can be used to determine ROIs for ablation at block 350 without using (e.g., viewing, analyzing) the combined maps/video 346.

In some embodiments, the quality map 332 is also used in combination with the combined Driver/Perpetuator Map 334 and/or the combined maps/video 346 to determine ROIs for ablation at block 350. The quality map 332 is used to determine the trustworthiness of the generated maps (e.g., driver map 328, perpetuator map 330 and driver/perpetuator map 334) related to AF substrate 314 and the generated maps (e.g., activation/wave maps 336, CV maps 338, fraction maps 340, voltage maps 342 and block maps 344) related to the AF Process 316 parameters. If the quality of the quality map is low, the generated maps are less trusted and appointing an ablation ROI (350) must be regarded with an increase level of care (e.g., by a physician) compared to when the quality map indicates high quality signals (IC ECGS) as the basis for the generated maps.

In some embodiments, determining ROIs for ablation at block 350 includes appointing or selecting one or more ablation sites for use in determining one or more ROIs for ablation. For example, ablation sites may be appointed or selected from driver evidence and perpetuator evidence (e.g., determined from the driver map 328, the perpetuator map 330 or the combined driver/perpetuator map 334) and ROIs may be determined based on the appointed sites.

The maps and mapping techniques disclosed herein potentially: (i) reduce AF map analysis training time; (ii) reduce time to determine ROIs for ablation; (iii) facilitate efficient interpretation of AF maps; and (iv) increase ablation success rates for ablation aimed at isolation and extinguishing of drivers, path lengthening, slowing of re-entry circuits, fibrillatory conduction and fractionated potentials.

Figure 4:
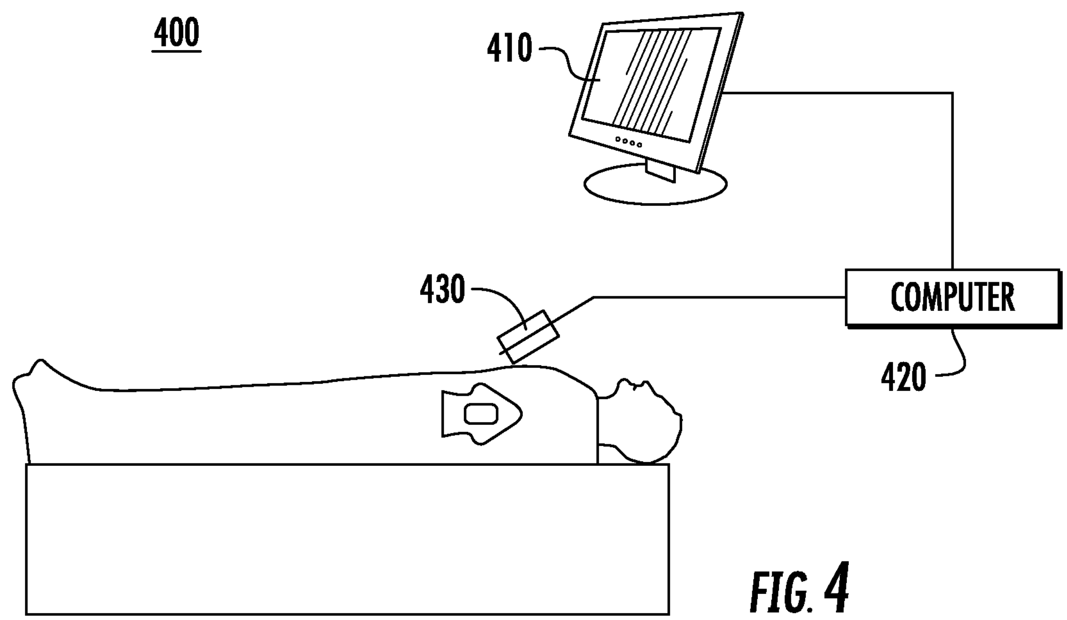
FIG. 4 is a schematic illustration of an exemplary mapping system for real-time mapping of cardiac ablation.

FIG. 4 is a schematic illustration of an exemplary mapping system 100 for real-time mapping of cardiac ablation in accordance with an embodiment of the present invention, in which the inventive apparatus is used. System 400 comprises a display 410 for displaying recorded signals, a computer 420, which preferably comprises appropriate signal processing circuits that are typically contained inside a housing of the computer 420. Computer 420 is preferably programmed in software and/or hardware to carry out the functions described herein. This software may be downloaded to the computer 420 in electronic form, over a network, for example, or it may alternatively be provided on tangible media, such as magnetic or optical media or other nonvolatile memory. In some embodiments, computer 420 comprises a general-purpose computer. The system 400 further comprises a probe or catheter 430.

A catheter adapted for endocardial mapping and ablating tissue from the atria includes a catheter body and an electrode assembly comprising a number of non-overlapping loops having a number of electrodes arranged in rows such that each row is separated by any number of degrees from the next row. In some embodiments, the non-overlapping loops may be concentric loops. The loops of the catheter may be of any number. For example, the catheter could be configured with 3 loops such that there are 3 electrodes in each row, where each row is separated by 90 degrees from the next row. In addition, the number of electrodes per row could be increased to 5 or more with 20 or more electrodes. The electrodes, in addition to having mapping capabilities, may also be configured to deliver RF to ablate tissue.

The configuration of the catheter and the electrode assembly may allow for faster mapping of the atria. This configuration may also provide coverage of the entire surface of the atrial chamber. The catheter may also allow the stage of complex processing and generation of activation maps to be skipped by providing instant information to the user via continuous display of the activation sequence. The configuration of the catheter may also allow the user to explore and locate the triggers/sources in a precise manner. The catheter and system may enable the user to build a reasonable strategy for RF application and monitor changes in activation in real time during ablation.

Figure 5:
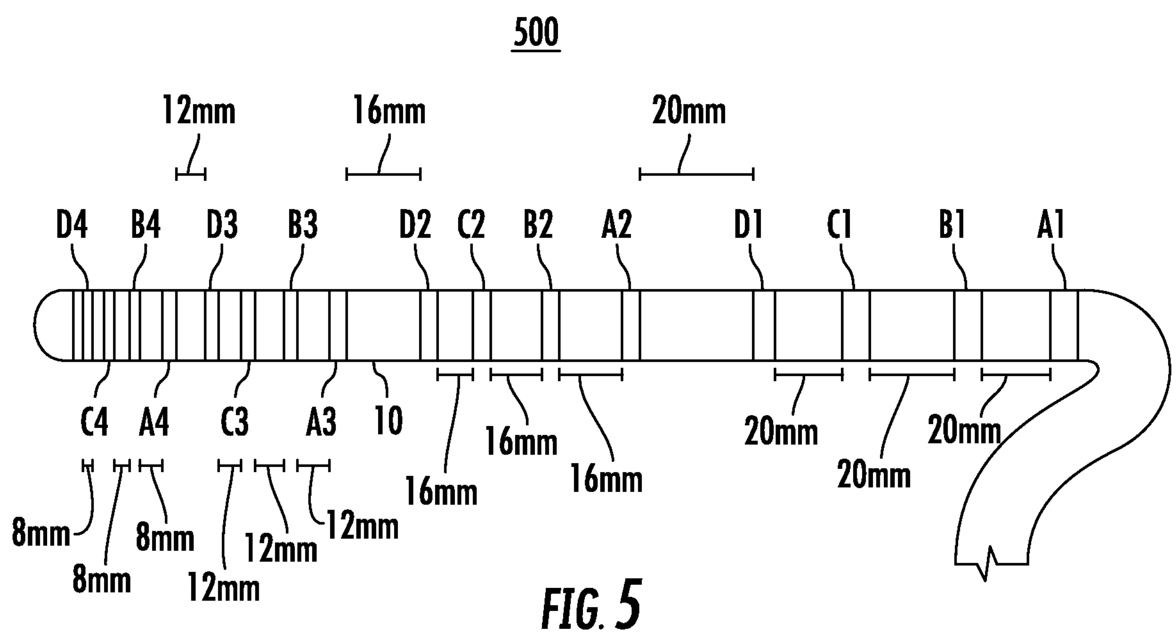
FIG. 5 is a top view diagram of an example catheter configured to map AF and identify activation sources for direct and focused treatment shown in elongated form.

FIG. 5 is a top view diagram of an example catheter 500 configured to map AF and identify activation sources for direct and focused treatment shown in elongated form. The catheter body 10 comprises an elongated tubular construction having a single, axial or central lumen. The catheter body 10 is flexible, i.e., bendable, but substantially non-compressible along its length. The catheter body 10 may be of any suitable construction and made of any suitable material. In one example construction, an outer wall of polyurethane or PEBAX may be used. In another example construction, an outer wall may comprise an embedded braided mesh of stainless steel or the like to increase torsional stiffness of the catheter body 10.

In this example, the 16 electrodes are distributed along the length of the catheter body 10. Electrodes A1, B1, C1, and D1 are configured to form an outermost loop when the catheter is coiled to form non-overlapping loops. Electrodes A1, B1, C1, and D1 are spaced further apart than electrodes A2, B2, C2, and D2, which form a next inner loop when the catheter is coiled to form non-overlapping loops. Electrodes A1, B1, C1, and D1 are configured so that they may substantially directly align with electrodes A2, B2, C2, and D2, respectively when forming non-overlapping loops. Electrodes A2, B2, C2, and D2 are spaced further apart than electrodes A3, B3, C3, and D3, which are configured to form a next inner loop when the catheter is coiled to form non-overlapping loops. Electrodes A3, B3, C3, and D3 are configured so that they may substantially directly align with electrodes A1, B1, C1, D1, respectively, and with electrodes A2, B2, C2, and D2, respectively when the catheter is coiled to form non-overlapping loops. Electrodes A3, B3, C3, and D3 are spaced further apart than electrodes A4, B4, C4, and D4, which are configured to form an innermost loop in this example. Electrodes A4, B4, C4, and D4 are configured so that they may substantially directly align with electrodes A1, B1, C1, D1, respectively, with electrodes A2, B2, C2, and D2, respectively, and with electrodes A3, B3, C3, and D3, respectively, when the catheter is coiled to form non-overlapping loops.

In this example, when the catheter is coiled to form non-overlapping loops, the diameter of the first loop may be approximately 25 mm, therefore the distance between each of the adjacent electrodes A1-B1, B1-C1, C1-D1, and D1-A2 may be approximately 20 mm. The diameter of the second loop may be approximately 20 mm, therefore the distance between each of the adjacent electrodes A2-B2, B2-C2, C2-D2, and D2-A3 may be approximately 16 mm. The diameter of the third loop may be approximately 15 mm, therefore the distance between each of the adjacent electrodes A3-B3, B3-C3, C3-D3, and D3-A4 may be approximately 12 mm. The diameter of the fourth loop may be approximately 10 mm, therefore the distance between each of the adjacent electrodes A4-B4, B4-C4, and C4-D4 may be approximately 8 mm.

Figure 6:
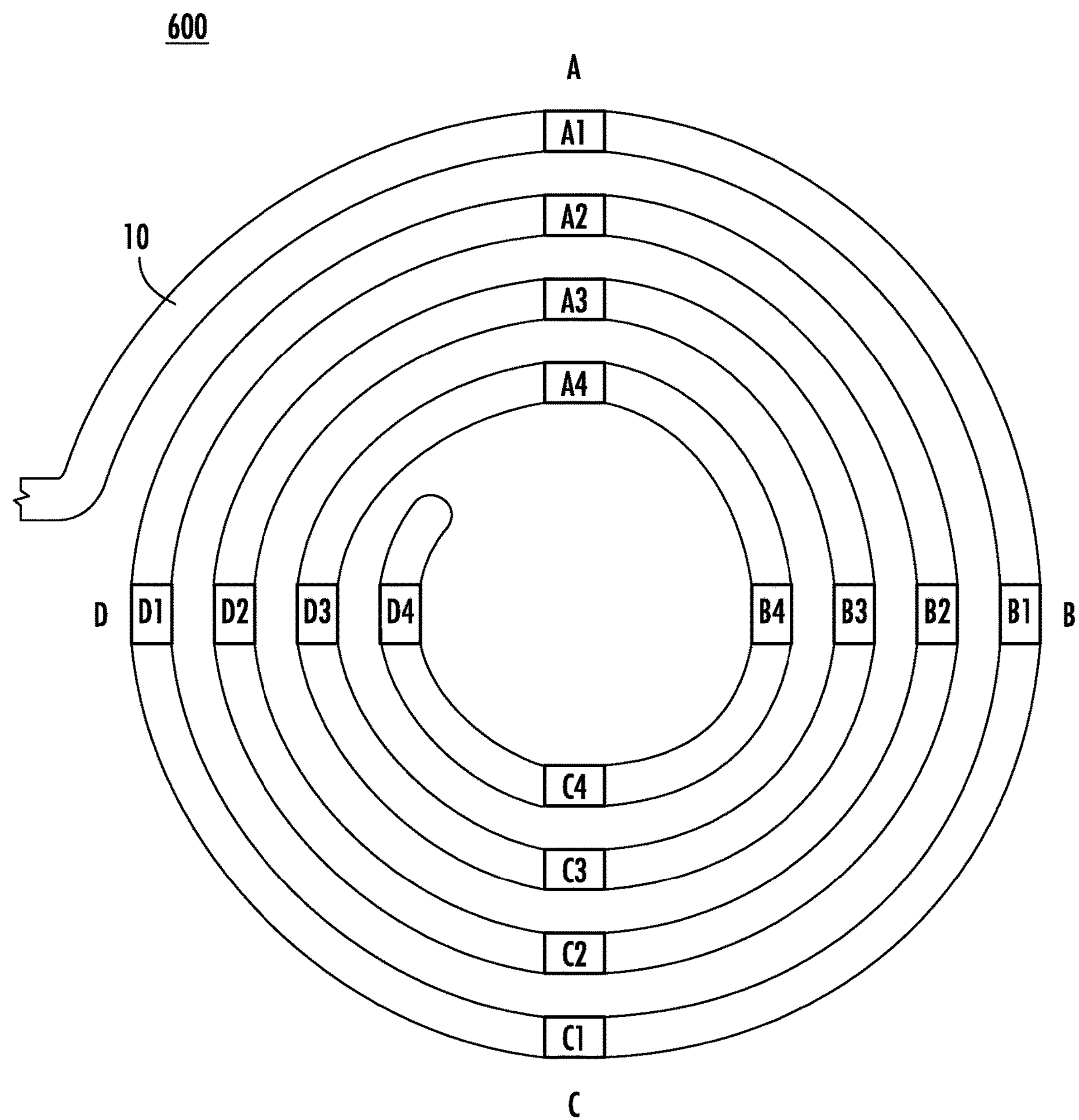
FIG. 6 is a top view diagram of the example catheter of FIG. 5 shown in a substantially flat coiled form.

FIG. 6 is a top view diagram of an example catheter 600, which is the example catheter of FIG. 5 shown in a substantially flat coiled form. In this example, the catheter 600 may comprise a catheter body 10 configured to form a circular shape upon exiting a sheath. In this example, only the circular end section of the catheter 600 is shown for simplicity. The catheter body 10 may be configured to form four non-overlapping loops having 16 electrodes such that the electrodes are arranged in four rows separated by 90 degrees between each pair of rows upon exiting the sheath. The catheter may be constructed such that the radius of each loop and the distance between consecutive electrodes determines the alignment of the rows of electrodes such that each row of electrodes is separated by 90 degrees from the next row of electrodes.

The circular end section of the catheter 600 may be fixed to the distal end of the catheter shaft. The circular end section of the catheter 600 may be resilient and formed so as to assume arcuate pre-shaped loops when the catheter 600 exits the sheath. Accordingly, the catheter 600 regains the pre-designed non-overlapping loops as it exits the sheath.

In this example, the 16 electrodes are distributed among four rows A, B, C, and D. Row A comprises electrodes A1, A2, A3, and A4, with electrode A1 located on the outermost loop. Each successive electrode A2, A3, and A4 are located on a respective inner loop, with electrode A4 being located on the innermost loop. The distance between electrodes in the same row is about 3 mm for a catheter having an outermost loop diameter of approximately 25 mm. Row B is separated by 90 degrees from row A and comprises electrodes B1, B2, B3, and B4, with electrode B1 located on the outermost loop. Each successive electrode B2, B3, and B4 are located on a respective inner loop, with electrode B4 being located on the innermost loop. Row C is separated by 90 degrees from row B and comprises electrodes C1, C2, C3, and C4, with electrode C1 located on the outermost loop. Each successive electrode C2, C3, and C4 are located on a respective inner loop, with electrode C4 being located on the innermost loop. Row D is separated by 90 degrees from row C and comprises electrodes D1, D2, D3, and D4, with electrode D1 located on the outermost loop. Each successive electrode D2, D3, and D4 are located on a respective inner loop, with electrode D4 being located on the innermost loop.

The distance between electrodes in the same row may be approximately 3 mm. For example, in row A, the distances between electrodes A1-A2, A2-A3, and A3-A4 may each be approximately 3 mm. In this example, the electrodes in rows B, C, and D would follow the same distance pattern as row A.

In this example, the diameter of the outermost loop may be approximately 25 mm, therefore the distance between each of the adjacent electrodes A1-B1, B1-C1, C1-D1, and D1-A2 may be approximately 20 mm. The diameter of the next inner loop may be approximately 20 mm, therefore the distance between each of the adjacent electrodes A2-B2, B2-C2, C2-D2, and D2-A3 may be approximately 16 mm. The diameter of the next inner loop may be approximately 15 mm, therefore the distance between each of the adjacent electrodes A3-B3, B3-C3, C3-D3, and D3-A4 may be approximately 12 mm. The diameter of the innermost loop may be approximately 10 mm, therefore the distance between each of the adjacent electrodes A4-B4, B4-C4, and C4-D4 may be approximately 8 mm.

Figure 7:
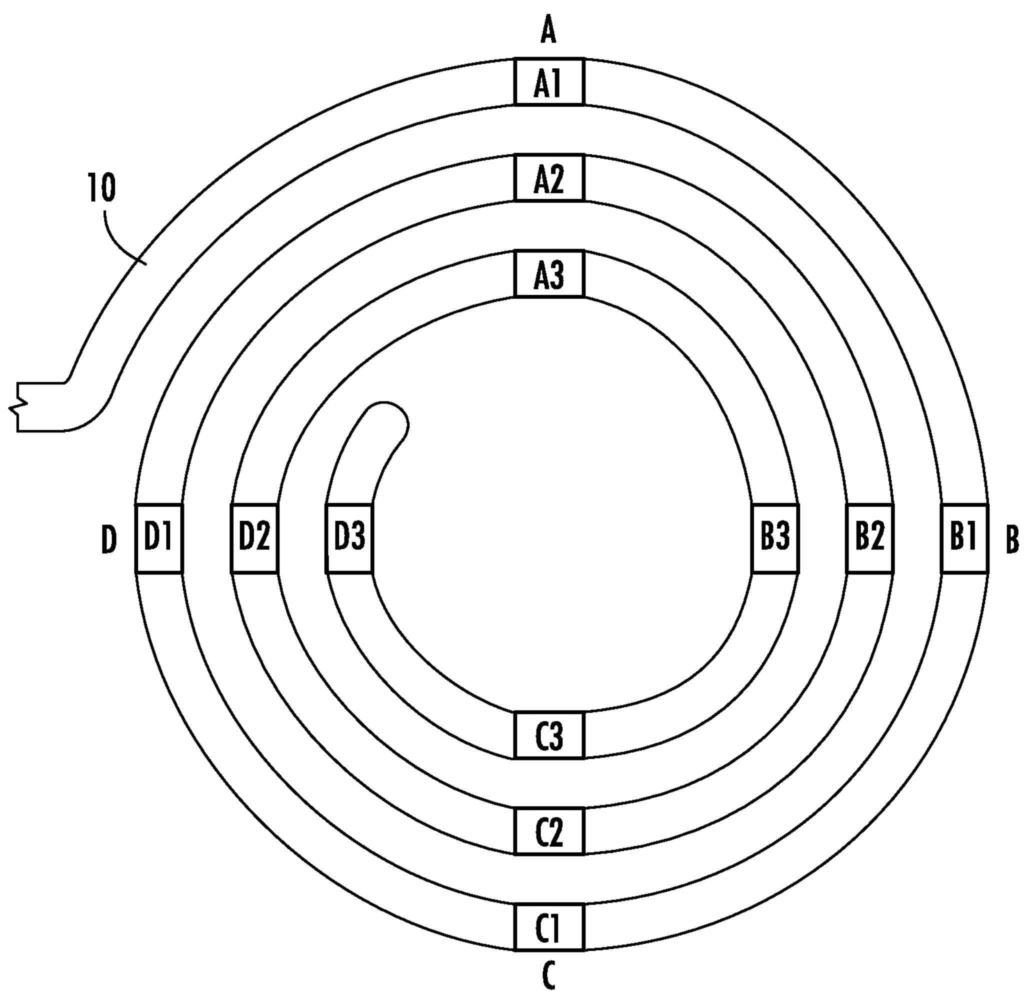
FIG. 7 is a top view diagram of an example catheter configured to map AF and identify activation sources for direct and focused treatment shown in a substantially flat coiled form with three non-overlapping loops.

FIG. 7 is a top view diagram of an example catheter 700 configured to map AF and identify activation sources for direct and focused treatment shown in a substantially flat coiled form with three non-overlapping loops. In this example, the catheter 700 may comprise a catheter body 10 configured to form a circular shape upon exiting a sheath. In this example, only the circular end section of the catheter 700 is shown for simplicity. The catheter body 10 may be configured to form three non-overlapping loops having 12 electrodes such that the electrodes are arranged in three rows separated by 90 degrees between each pair of rows. The catheter may be constructed such that the radius of each loop and the distance between consecutive electrodes determines the alignment of the rows of electrodes such that each row of electrodes is separated by 90 degrees from the next row of electrodes.

The circular end section of the catheter 700 may be fixed to the distal end of the catheter shaft. The circular end section of the catheter 700 may be resilient and formed so as to assume arcuate pre-shaped loops when the catheter 700 exits the sheath. Accordingly, the catheter 700 regains the pre-designed non-overlapping loops as it exits the sheath.

In this example, the 12 electrodes are distributed among three rows A, B, and C. Row A comprises electrodes A1, A2, and A3, with electrode A1 located on the outermost loop. Each successive electrode A2 and A3 are located on a respective inner loop, with electrode A3 being located on the innermost loop. Row B is separated by 90 degrees from row A and comprises electrodes B1, B2, and B3, with electrode B1 located on the outermost loop. Each successive electrode B2 and B3 are located on a respective inner loop, with electrode B3 being located on the innermost loop. Row C is separated by 90 degrees from row B and comprises electrodes C1, C2, and C3, with electrode C1 located on the outermost loop. Each successive electrode C2 and C3 are located on a respective inner loop, with electrode C3 being located on the innermost loop. Row D is separated by 90 degrees from row C and comprises electrodes D1, D2, and D3 with electrode D1 located on the outermost loop. Each successive electrode D2 and D3 are located on a respective inner loop, with electrode D3 being located on the innermost loop.

The distance between electrodes in the same row may be approximately 3 mm. For example, in row A, the distances between electrodes A1-A2 and A2-A3 may each be approximately 3 mm. In this example, the electrodes in rows B, C, and D would follow the same distance pattern as row A.

In this example, the diameter of the outermost loop may be approximately 20 mm, therefore the distance between each of the adjacent electrodes A1-B1, B1-C1, C1-D1, and D1-A2 may be approximately 16 mm. The diameter of the next inner loop may be approximately 15 mm, therefore the distance between each of the adjacent electrodes A2-B2, B2-C2, C2-D2, and D2-A3 may be approximately 12 mm. The diameter of the innermost loop may be approximately 10 mm, therefore the distance between each of the adjacent electrodes A3-B3, B3-C3, and C3-D3 may be approximately 8 mm.

Figure 8:
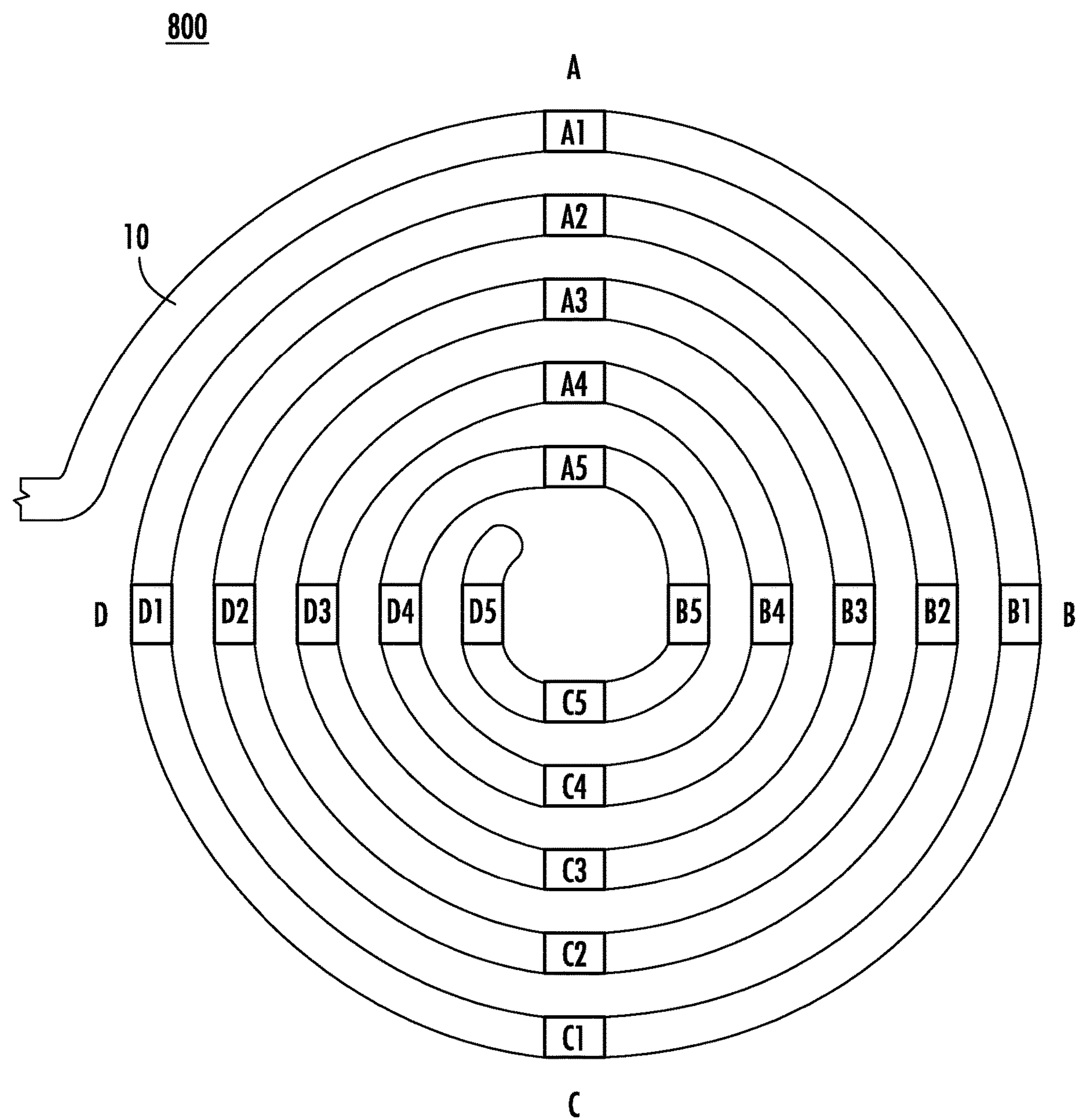
FIG. 8 is a top view diagram of an example catheter configured to map AF and identify activation sources for direct and focused treatment shown in a substantially flat coiled form with five non-overlapping loops.

FIG. 8 is a top view diagram of an example catheter 800 configured to map AF and identify activation sources for direct and focused treatment shown in a substantially flat coiled form with five non-overlapping loops. In this example, only the circular end section of the catheter 800 is shown for simplicity. The catheter 800 may comprise a catheter body 10 configured to form a circular shape upon exiting a sheath. The catheter body 10 may be configured to form five non-overlapping loops having 20 electrodes such that the electrodes are arranged in four rows separated by 90 degrees between each pair of rows. The catheter may be constructed such that the radius of each loop and the distance between consecutive electrodes determines the alignment of the rows of electrodes such that each row of electrodes is separated by 90 degrees from the next row of electrodes.

The circular end section of the catheter 800 may be fixed to the distal end of the catheter shaft. The circular end section of the catheter 800 may be resilient and formed so as to assume arcuate pre-shaped loops when the catheter 800 exits the sheath. Accordingly, the catheter 800 regains the pre-designed non-overlapping loops as it exits the sheath.

In this example, the 20 electrodes are distributed among four rows A, B, C, and D. Row A comprises electrodes A1, A2, A3, A4, and A5, with electrode A1 located on the outermost loop. Each successive electrode A2, A3, A4, and A5 are located on a respective inner loop, with electrode A5 being located on the innermost loop. Row B is separated by 90 degrees from row A and comprises electrodes B1, B2, B3, B4, and B5, with electrode B1 located on the outermost loop. Each successive electrode B2, B3, B4, and B5 are located on a respective inner loop, with electrode B5 being located on the innermost loop. Row C is separated by 90 degrees from row B and comprises electrodes C1, C2, C3, C4, and C5, with electrode C1 located on the outermost loop. Each successive electrode C2, C3, C4, and C5 are located on a respective inner loop, with electrode C5 being located on the innermost loop. Row D is separated by 90 degrees from row C and comprises electrodes D1, D2, D3, D4, and D5, with electrode D1 located on the outermost loop. Each successive electrode D2, D3, D4, and D5 are located on a respective inner loop, with electrode D5 being located on the innermost loop.

The distance between electrodes in the same row may be approximately 3 mm. For example, in row A, the distances between electrodes A1-A2, A2-A3, A3-A4, and A4-A5 may each be approximately 3 mm. In this example, the electrodes in rows B, C, and D would follow the same distance pattern as row A.

In this example, the diameter of the outermost loop may be approximately 30 mm, therefore the distance between each of the adjacent electrodes A1-B1, B1-C1, C1-D1, and D1-A2 may be approximately 24 mm. The diameter of the next inner loop may be approximately 25 mm, therefore the distance between each of the adjacent electrodes A2-B2, B2-C2, C2-D2, and D2-A3 may be approximately 20 mm. The diameter of the next inner loop may be approximately 20 mm, therefore the distance between each of the adjacent electrodes A3-B3, B3-C3, C3-D3, and D3-A4 may be approximately 16 mm. The diameter of the next inner loop may be approximately 15 mm, therefore the distance between each of the adjacent electrodes A4-B4, B4-C4, C4-D4, and D4-A5 may be approximately 12 mm. The diameter of the innermost loop may be approximately 10 mm, therefore the distance between each of the adjacent electrodes A5-B5, B5-C5, and C5-D5 may be approximately 8 mm.

Figure 9:
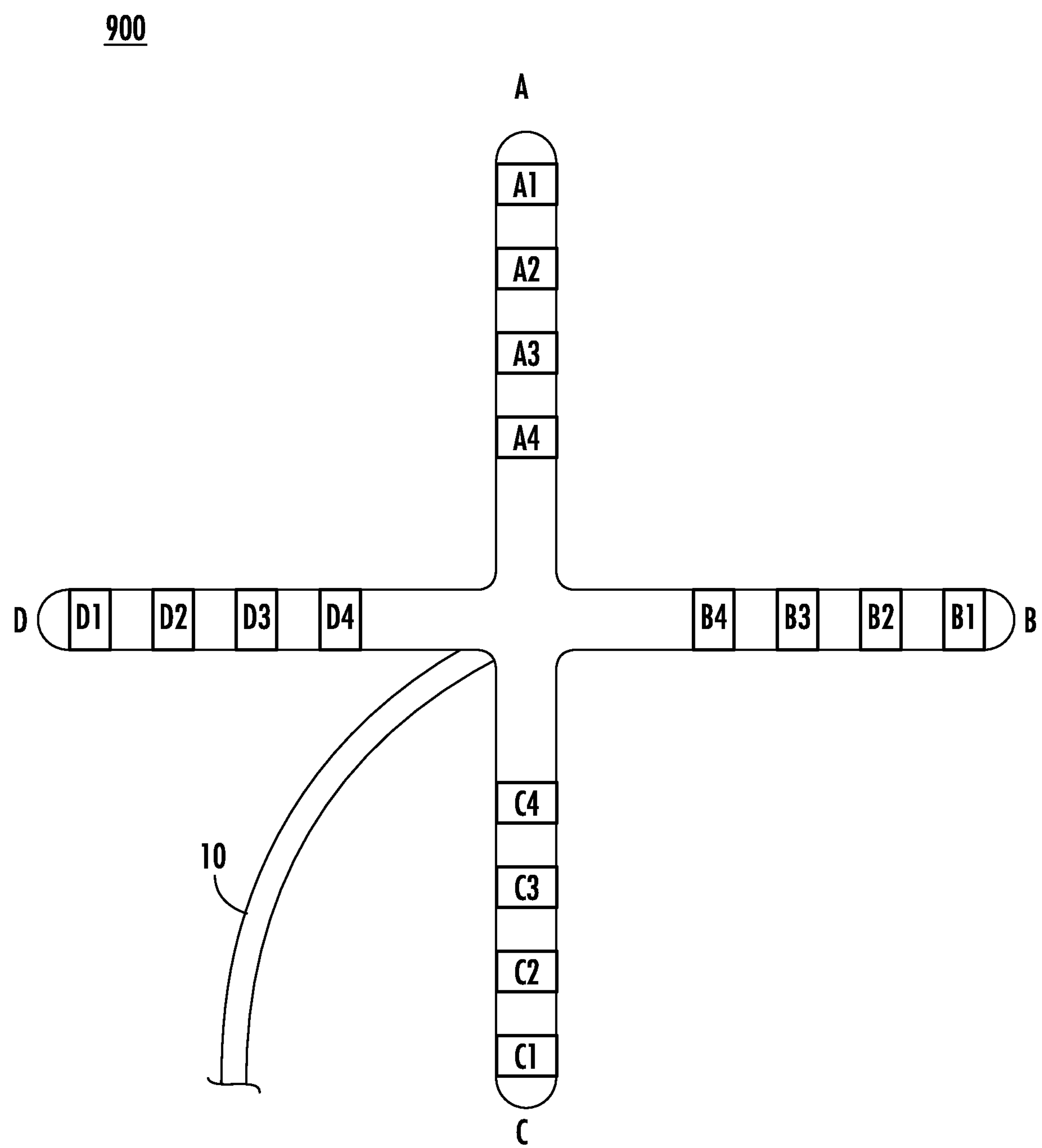
FIG. 9 is a top view diagram of an example catheter configured to map AF and identify activation sources for direct and focused treatment shown in a cross-shaped spline configuration.

FIG. 9 is a top view diagram of an example catheter 900 configured to map AF and identify activation sources for direct and focused treatment shown in a cross-shaped spline configuration. In this example, the catheter 600 may comprise a catheter body 10 configured to form a cross-shaped spline configuration upon exiting a sheath. This example cross-shaped spline configuration includes four splines arranged in a cross pattern such that each spline is separated by 90 degrees from the next spline.

In this example, each spline A, B, C, and D are configured to have four electrodes. For example, spline A comprises electrodes A1, A2, A3, and A4, with electrode A1 being the outermost electrode. Each successive electrode is located more inward than the previous electrode with electrode A4 being the innermost electrode. Spline B is separated by 90 degrees from spline A and comprises electrodes B1, B2, B3, and B4, with electrode B1 being the outermost electrode. Each successive electrode is located more inward than the previous electrode with electrode B4 being the innermost electrode. Spline C is separated by 90 degrees from spline B and comprises electrodes C1, C2, C3, and C4, with electrode C1 being the outermost electrode. Each successive electrode is located more inward than the previous electrode with electrode C4 being the innermost electrode. Spline D is separated by 90 degrees from spline C and comprises electrodes D1, D2, D3, and D4, with electrode D1 being the outermost electrode. Each successive electrode is located more inward than the previous electrode with electrode D4 being the innermost electrode.

The distance between electrodes in the same row may be approximately 3 mm. For example, in row A, the distances between electrodes A1-A2, A2-A3, and A3-A4 may each be approximately 3 mm. In this example, the electrodes in rows B, C, and D would follow the same distance pattern as row A.

The catheter body 10 may be configured to include any number of splines, and each spline may contain any number of electrodes. In an example where the catheter is configured with less than four splines, each spline may be arranged such that it is separated from the next spline by more than 90 degrees. Conversely, in an example where the catheter is configured with more than four splines, each spline may be arranged such that it is separated from the next spline by less than 90 degrees.

Figure 10:
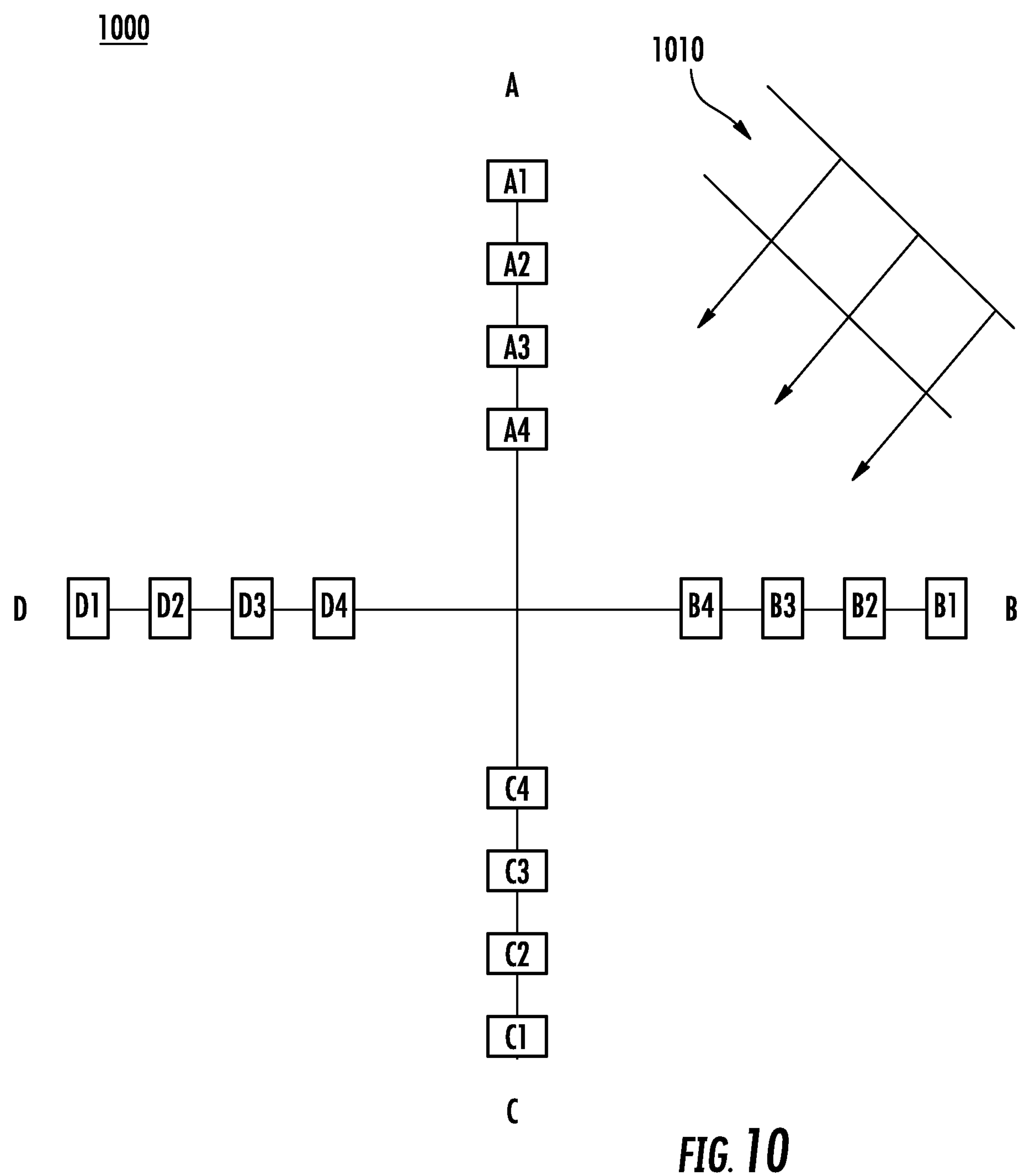
FIG. 10 is a diagram of an example electrode configuration that may be used to identify a wave front direction of activation to determine the origin of activation for a single wide activation pattern.

FIG. 10 is a diagram of an example electrode configuration 1000 that may be used to identify a wave front direction of activation to determine the origin of activation for a single wide activation pattern. In this example, as a wave front 1010 approaches the catheter, the outermost electrodes A1 and B1 detect the wave front 1010 and activate substantially simultaneously. The activation of electrodes A1 and B1 are recorded in the system as recorded signals. As the wave front 1010 continues its path, electrodes A2 and B2 next detect the wave front 1010 and activate substantially simultaneously. The activation of electrodes A2 and B2 are then recorded in the system as recorded signals. Following the activation of electrodes A2 and B2, electrodes A3 and B3 detect the wave front 1010 and activate substantially simultaneously. The activation of electrodes A3 and B3 are recorded in the system as recorded signals. Following the activation of electrodes A3 and B3, electrodes A4 and B4 detect the wave front 1010 and activate substantially simultaneously. The activation of electrodes A4 and B4 are recorded in the system as recorded signals. Following the activation of electrodes A4 and B4, electrodes C4 and D4 detect the wave front 1010 and activate substantially simultaneously. The activation of electrodes C4 and D4 are recorded in the system as recorded signals. Following the activation of electrodes C4 and D4, electrodes C3 and D3 detect the wave front 1010 and activate substantially simultaneously. The activation of electrodes C3 and D3 are recorded in the system as recorded signals. Following the activation of electrodes C3 and D3, electrodes C2 and D2 detect the wave front 1010 and activate substantially simultaneously. The activation of electrodes C2 and D2 are recorded in the system as recorded signals. Following the activation of electrodes C2 and D2, electrodes C1 and D1 detect the wave front 1010 and activate substantially simultaneously. The activation of electrodes C1 and D1 are recorded in the system as recorded signals.

Figure 11:
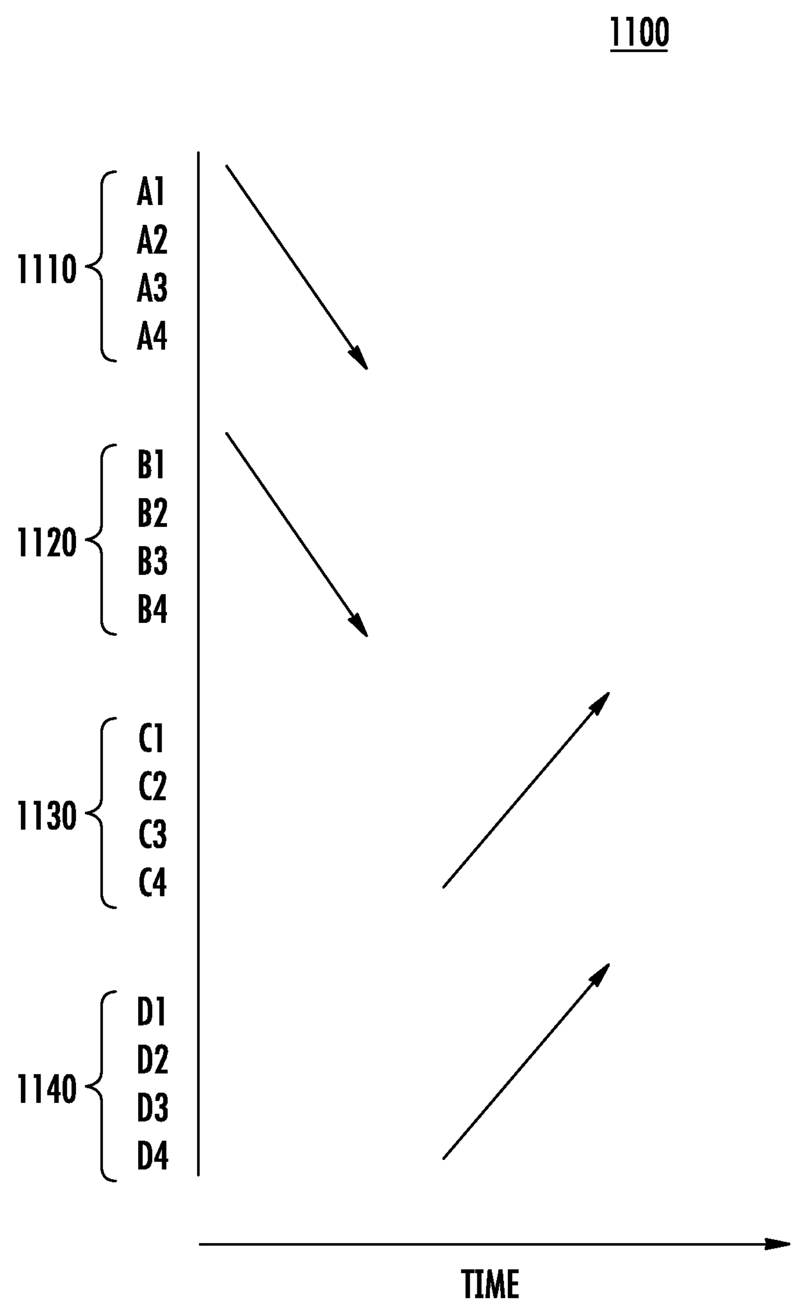
FIG. 11 is a diagram of an example of recorded signals from a catheter based on the electrode activation times for a single wide activation pattern.

FIG. 11 is a diagram of an example of recorded signals 1100 from a catheter with an electrode configuration of FIG. 10. The recorded signals 1100 from the catheter in this example are based on the electrode activation times for a single wide activation pattern. The recorded signals from the catheter are arranged in a specific configuration to easily enable the identification of a wave front direction of activation to determine the origin of activation. The recorded signals may be arranged according to predefined templates or configurations that may be manually changed by the user or automatically updated by the system by using an algorithm to display the optimal configuration based on the sequence of activation along each of the electrodes' rows.

Referring to FIG. 11, the recorded signals 1100 are arranged based on electrode activation times and displayed on a display. Electrode set A 1110 comprises electrodes A1, A2, A3, and A4. Electrode set B 1120 comprises electrodes B1, B2, B3, and B4. Electrode set C 1130 comprises electrodes C 1, C2, C3, and C4. Electrode set D 1140 comprises electrodes D1, D2, D3, and D4. The electrode activation pattern for electrode set A 1110 and electrode set B 1120 show that the wave front 1010 is moving from the outer electrodes to the inner electrodes. Conversely, the electrode activation pattern for electrode set C 1130 and electrode set D 1140 show that the wave front 1010 is moving from the inner electrodes to the outer electrodes. Based on this information and the arrangement of recorded signals 1100, the system may determine that wave front 1010 is a single wide activation pattern.

In addition to determining the type of wave front, the arrangement of the recorded signals may be used to determine the direction of the activation origin. For example, the user may move the catheter to a new location toward the indicated direction of the activation of origin. At the new location, the system will again determine the direction of the activation origin to enable the user to determine the next movement. The user may then continue to move the catheter until reaching and determining the origin of activation. The origin of activation may be identified by pre-defined activation patterns, for example the single wide activation pattern shown in FIG. 8. The determination of the location and identifying the mechanism of the activation origins (i.e., triggers) are performed automatically by the system and may be confirmed by a visual review of the sequence of recorded signals at the location. The arrangement and density of the electrodes on the catheter will enable precise location of a focal activation, rotational activation, and determination of a re-entry pathway.

Figure 12:
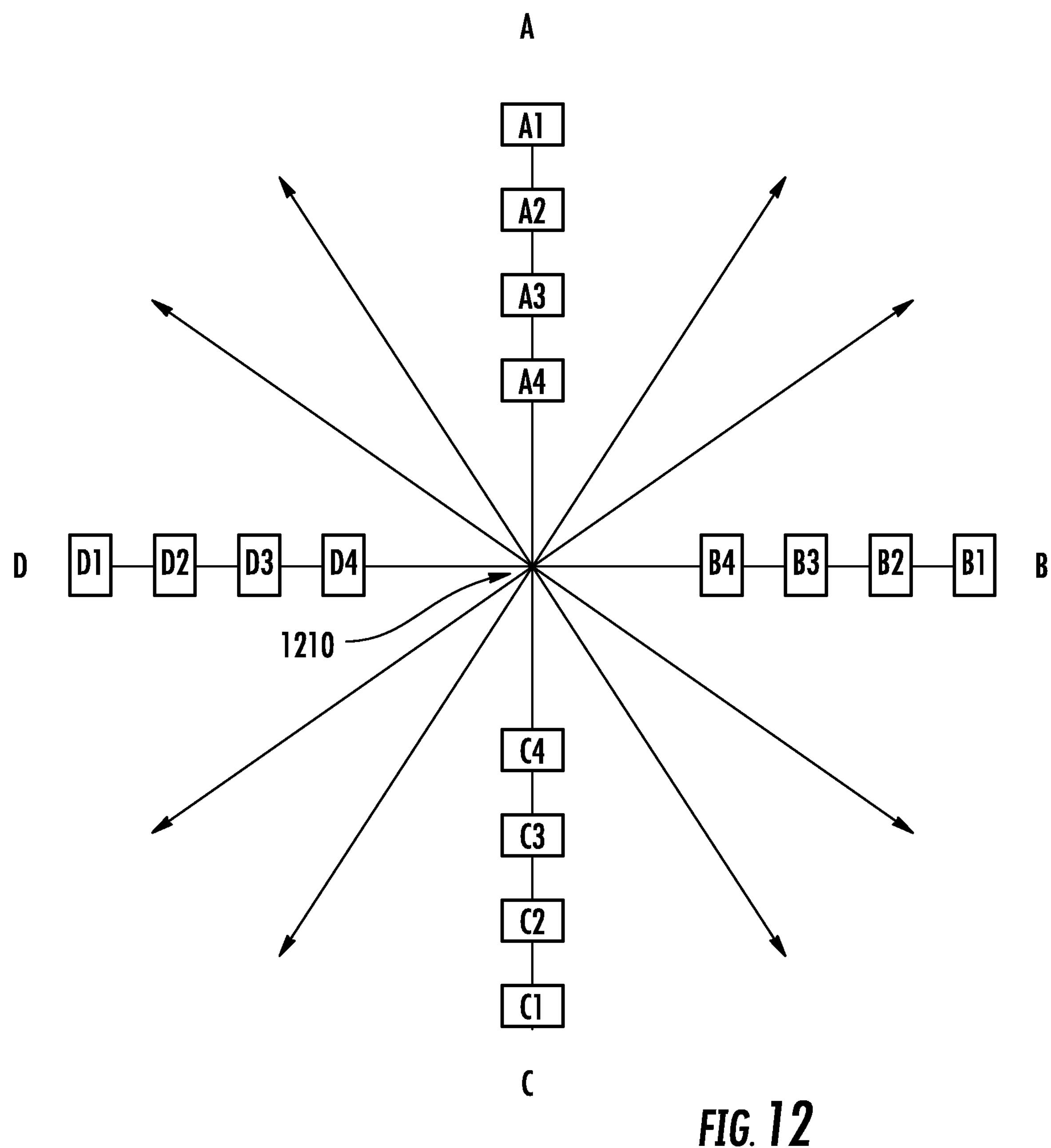
FIG. 12 is a diagram of an example electrode configuration that may be used to identify a wave front direction of activation to determine the origin of activation for a focal activation pattern.

FIG. 12 is a diagram of an example electrode configuration 1200 that may be used to identify a wave front direction of activation to determine the origin of activation for a focal activation pattern. In this example, as a wave front 1210 approaches the catheter, the innermost electrodes A4, B4, C4, and D4 detect the wave front 1210 and activate substantially simultaneously. The activation of electrodes A4, B4, C4, and D4 are recorded in the system as recorded signals. As the wave front 1210 continues its path, electrodes A3, B3, C3, and D3 detect the wave front 1210 and activate substantially simultaneously. The activation of electrodes A3, B3, C3, and D3 are recorded in the system as recorded signals. Following the activation of electrodes A3, B3, C3, and D3, electrodes A2, B2, C2, and D2 detect the wave front 1210 and activate substantially simultaneously. The activation of electrodes A2, B2, C2, and D2 are recorded in the system as recorded signals. Following the activation of electrodes A2, B2, C2, and D2, electrodes A1, B1, C1, and D1 detect the wave front 1210 and activate substantially simultaneously. The activation of electrodes A1, B1, C1, and D1 are recorded in the system as recorded signals.

Figure 13:
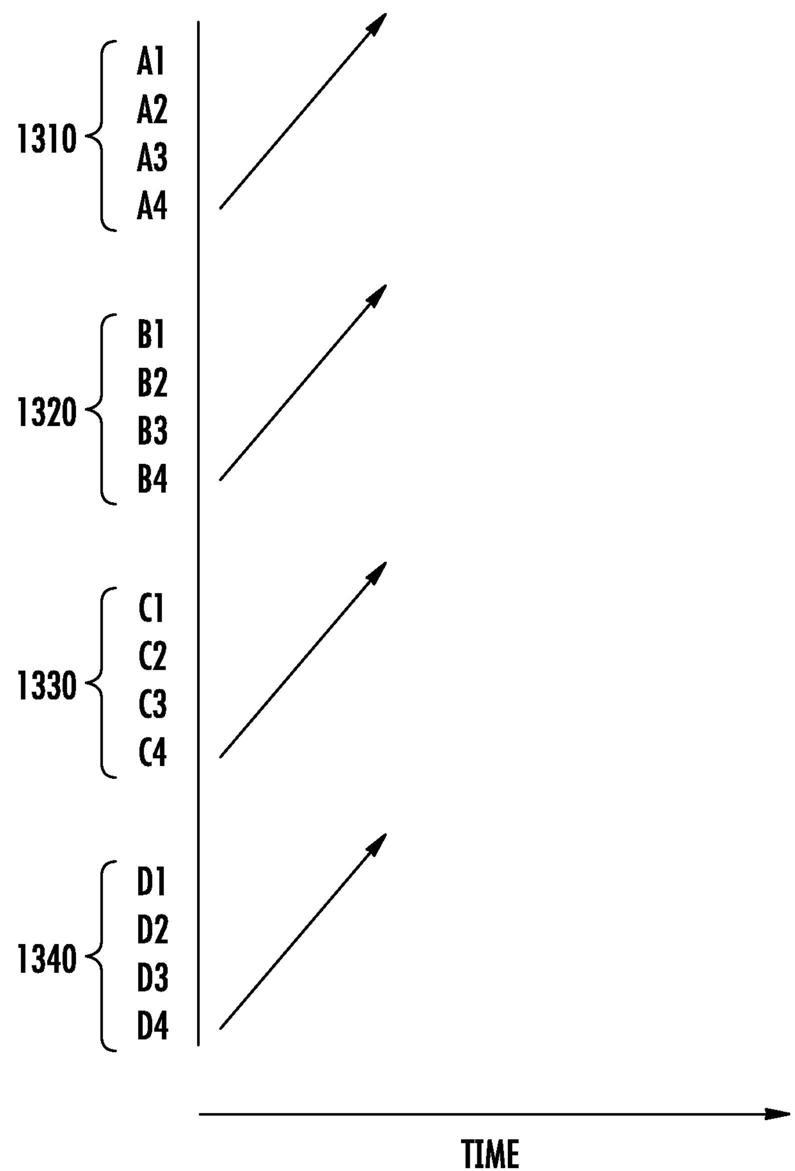
FIG. 13 is a diagram of an example of recorded signals from a catheter based on the electrode activation times for a focal activation pattern.

FIG. 13 is a diagram of an example of recorded signals 1300 from a catheter with an electrode configuration of FIG. 9. The recorded signals 1300 from the catheter in this example are based on the electrode activation times for a focal activation pattern. The recorded signals from the catheter are arranged in a specific configuration to easily enable the identification of the wave front direction of activation to determine the origin of activation. The recorded signals may be arranged according to predefined templates or configurations that may be manually changed by the user or automatically updated by the system by using an algorithm to display the optimal configuration based on the sequence of activation along each of the electrodes' rows.

Referring to FIG. 13, the recorded signals 1300 are arranged based on electrode activation times and may be displayed on a display. Electrode set A 1310 comprises electrodes A1, A2, A3, and A4. Electrode set B 1320 comprises electrodes B1, B2, B3, and B4. Electrode set C 1330 comprises electrodes C1, C2, C3, and C4. Electrode set D 1340 comprises electrodes D1, D2, D3, and D4. The electrode activation pattern for electrode set A 1310, electrode set B 1320, electrode set C 1330, and electrode set D 1340 show that the wave front 1210 is moving from the inner electrodes to the outer electrodes. Based on this information and the arrangement of recorded signals 1300, the system may determine that wave front 910 is a focal activation pattern and that the catheter is at the origin of activation.

In addition to determining the type of wave front, the arrangement of the recorded signals may be used to determine the direction of the activation origin. The system may be configured to indicate the direction of the activation. For example, the user may move the catheter to a new location toward the indicated direction of the activation of origin. Examples of the indications include, but are not limited to, highlighting and displaying the catheter electrodes of the earliest activation, highlighting and displaying the IC ECG channel with the earliest activation in the real time monitor of the EGM, or displaying the wave front of the activation on the anatomical map and/or image of the atria. At the new location, the system will again determine the direction of the activation origin to enable the user to determine the next movement. The user may then continue to move the catheter until reaching and determining the origin of activation. The origin of activation may be identified by pre-defined activation patterns, for example the focal activation pattern shown in FIG. 13. The determination of the location and identifying the mechanism of the activation origins (i.e., triggers) are performed automatically by the system and may be confirmed by a visual review of the sequence of recorded signals at the location. The arrangement and density of the electrodes on the catheter will enable precise location of a focal activation, rotational activation, and determination of a re-entry pathway.

Figure 14:
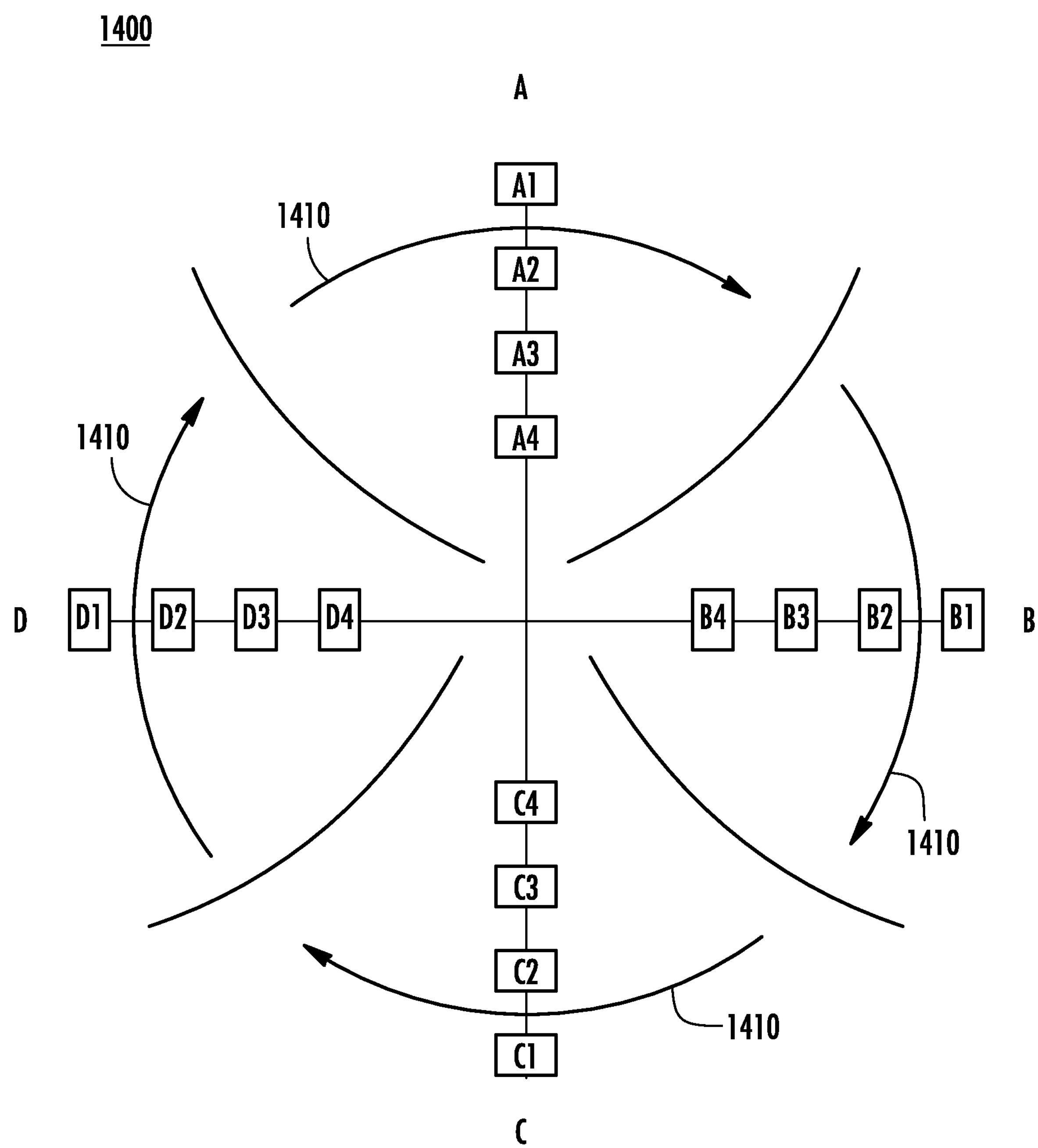
FIG. 14 is a diagram of an example electrode configuration that may be used to identify a wave front direction of activation to determine the origin of activation for a rotational activation pattern.

FIG. 14 is a diagram of an example electrode configuration 1400 that may be used to identify a wave front direction of activation to determine the origin of activation for a rotational activation pattern. In this example, the activation sequence of electrodes may occur in a circular or rotational pattern. For example, as a wave front 1410 approaches the catheter, electrodes A1, A2, A3, and A4 detect the wave front 1410 and activate substantially simultaneously. The activation of electrodes A1, A2, A3, and A4 are recorded in the system as recorded signals. As the wave front 1410 continues its path, electrodes B1, B2, B3, and B4 detect the wave front 1410 and activate substantially simultaneously. The activation of electrodes B1, B2, B3, and B4 are recorded in the system as recorded signals. The activation of electrodes B1, B2, B3, and B4 are recorded in the system as recorded signals. Following the activation of electrodes B1, B2, B3, and B4, electrodes C1, C2, C3, and C4 detect the wave front 1410 and activate substantially simultaneously. The activation of electrodes C1, C2, C3, and C4 are recorded in the system as recorded signals. Following the activation of electrodes C1, C2, C3, and C4, electrodes D1, D2, D3, and D4 detect the wave front 1410 and activate substantially simultaneously. The activation of electrodes D1, D2, D3, and D4 are recorded in the system as recorded signals. In this example, a rotational pattern of the outer circle may cover most of the cycle length (CL). As the catheter is moved toward the center of the rotational activity, a shortening of the rotational pattern may be observed.

Figure 15:
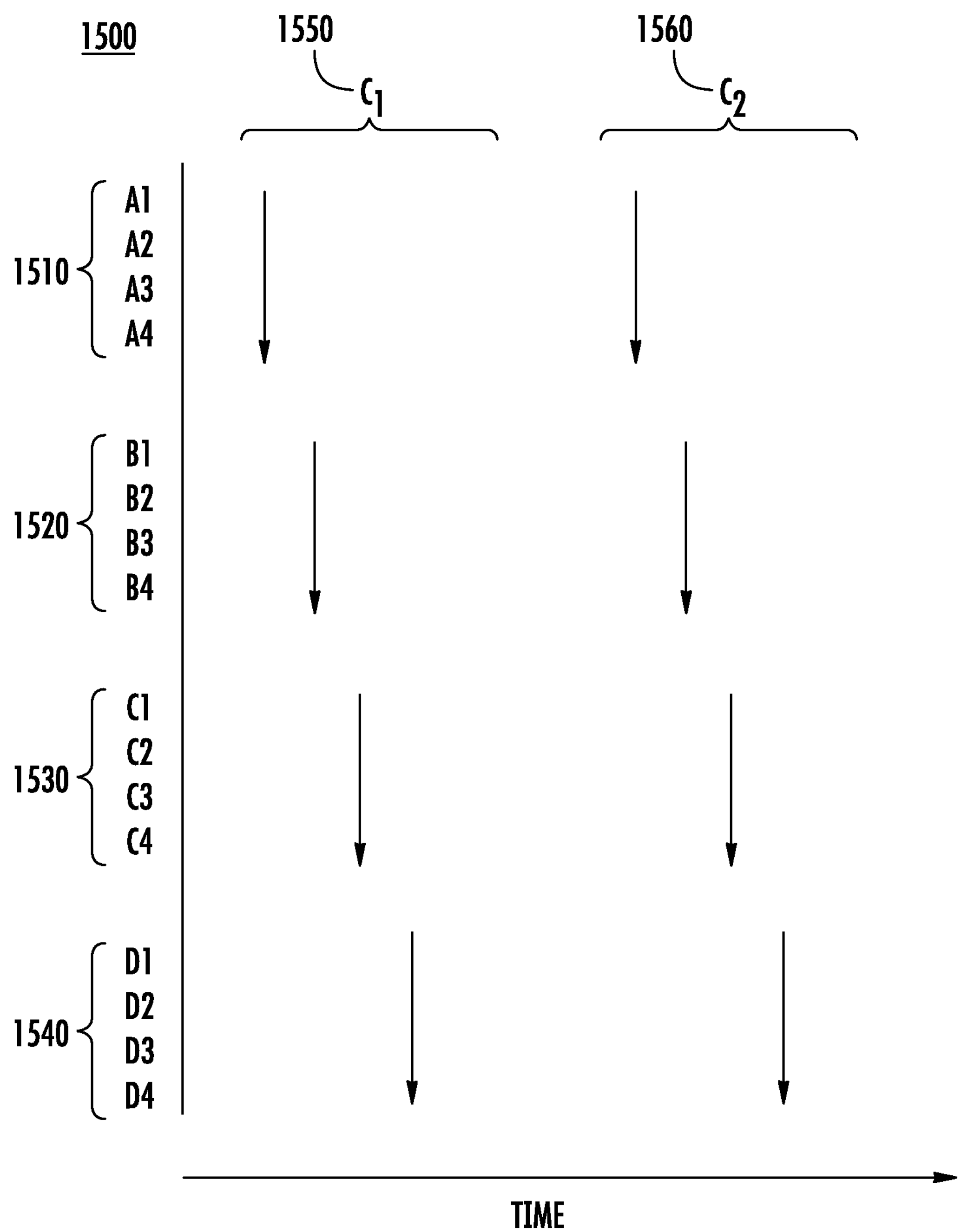
FIG. 15 is a diagram of an example of recorded signals from a catheter based on the electrode activation times for a rotational activation pattern.

FIG. 15 is a diagram of an example of recorded signals 1500 from a catheter with an electrode configuration of FIG. 14. The recorded signals 1500 from the catheter in this example are based on the electrode activation times for a rotational activation pattern and may be displayed on a display. In this example, electrode set A 1510 comprises electrodes A1, A2, A3, and A4. Electrode set B 1520 comprises electrodes B1, B2, B3, and B4. Electrode set C 1530 comprises electrodes C1, C2, C3, and C4. Electrode set D 1540 comprises electrodes D1, D2, D3, and D4. Although an unlimited number of cycles may be shown, in this example, two cycles of rotational activity are shown as $C_1$ 1550 and $C_2$ 1560 for simplicity. In the first cycle $C_1$ 1550, the wave front 1410 substantially simultaneously activates all the electrodes in electrode set A 1510 and the activation of the electrodes in electrode set A 1510 is recorded in the system as recorded signals. As the wavefront 1410 moves along its rotational path, it substantially simultaneously activates all the electrodes in electrode set B 1520 and the activation of the electrodes in electrode set B 1520 is recorded in the system as recorded signals. The wave front 1410 then continues along its rotational path and substantially simultaneously activates all the electrodes in electrode set C 1530 before then finally substantially simultaneously activating electrode set D 1540. The activation of the electrodes in electrode set C 1530 and electrode set D 1540 are respectively recorded in the system as recorded signals. This activation cycle then repeats in $C_2$ 1560. Based on this information and the arrangement of recorded signals 1500, the system may determine that wave front 1410 is a rotational activation pattern and that the catheter is at the origin of activation.

Figure 16:
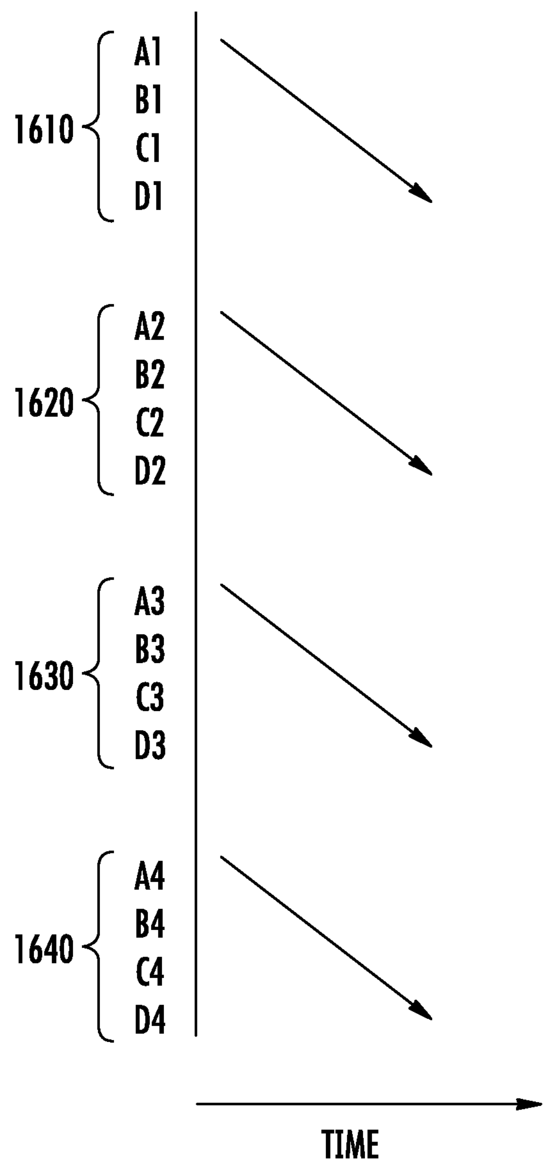
FIG. 16 is a diagram of another example of recorded signals from a catheter based on the electrode activation times for a rotational activation pattern.

FIG. 16 is a diagram of another example of recorded signals 1600 from a catheter with an electrode configuration of FIG. 14. The recorded signals 1600 from the catheter in this example are based on the electrode activation times for a rotational activation pattern and may be displayed on a display. In this example, the same data of FIG. 15 is displayed in an alternate configuration. In this example, the recorded signals 1600 may be arranged according to a predefined template or configuration that may be manually changed by the user or automatically updated by using an algorithm to display the optimal configuration based on the sequence of activation along each of the electrodes' rows.

Referring to FIG. 16, electrode set 1 1610 comprises electrodes A1, B1, C1, and D1. Electrode set 2 1620 comprises electrodes A2, B2, C2, and D2. Electrode set 3 1630 comprises electrodes A3, B3, C3, and D3. Electrode set 4 1640 comprises electrodes A4, B4, C4, and D4. In this example the wave front 1410 substantially simultaneously activates electrodes A1, A2, A3, and A4 and the activation of these electrodes is recorded in the system as recorded signals. As the wavefront 1410 moves along its rotational path, it substantially simultaneously activates electrodes B1, B2, B3, and B4 and the activation of these electrodes is recorded in the system as recorded signals. The wave front 1410 then continues along its rotational path and substantially simultaneously activates electrodes C1, C2, C3, and C4 before then finally substantially simultaneously activating electrodes D1, D2, D3, and D4. The activation of electrodes C1, C2, C3, and C4, and electrodes D1, D2, D3, and D4 are respectively recorded in the system as recorded signals.

A method of mapping may be based on the concept of identifying the activation sequence at any point or location and tracing the origin of the activation. The recorded signals by the catheter may be arranged in a specific configuration to enable the identification of the wave front direction of activation and determine the origin.

The system may use the method to indicate a direction of the activation origin to direct the user to move the catheter to a new location. At the new location, the system may again determine the direction of the activation origin to further direct the user to move the catheter towards the activation origin. The activation of origin may be identified based on predefined activation patterns, for example the activation patterns shown in FIG. 11, FIG. 13, FIG. 15, and FIG. 16. The system may alert the user upon reaching the origin of activation. The alert may be an audio alert, haptic alert, or a visual alert shown on a display. The determination of the location and identifying the mechanism of activation origins and triggers may be performed automatically by the system. The user may confirm by visually reviewing the sequence of recorded signals at the location.

Figure 17:
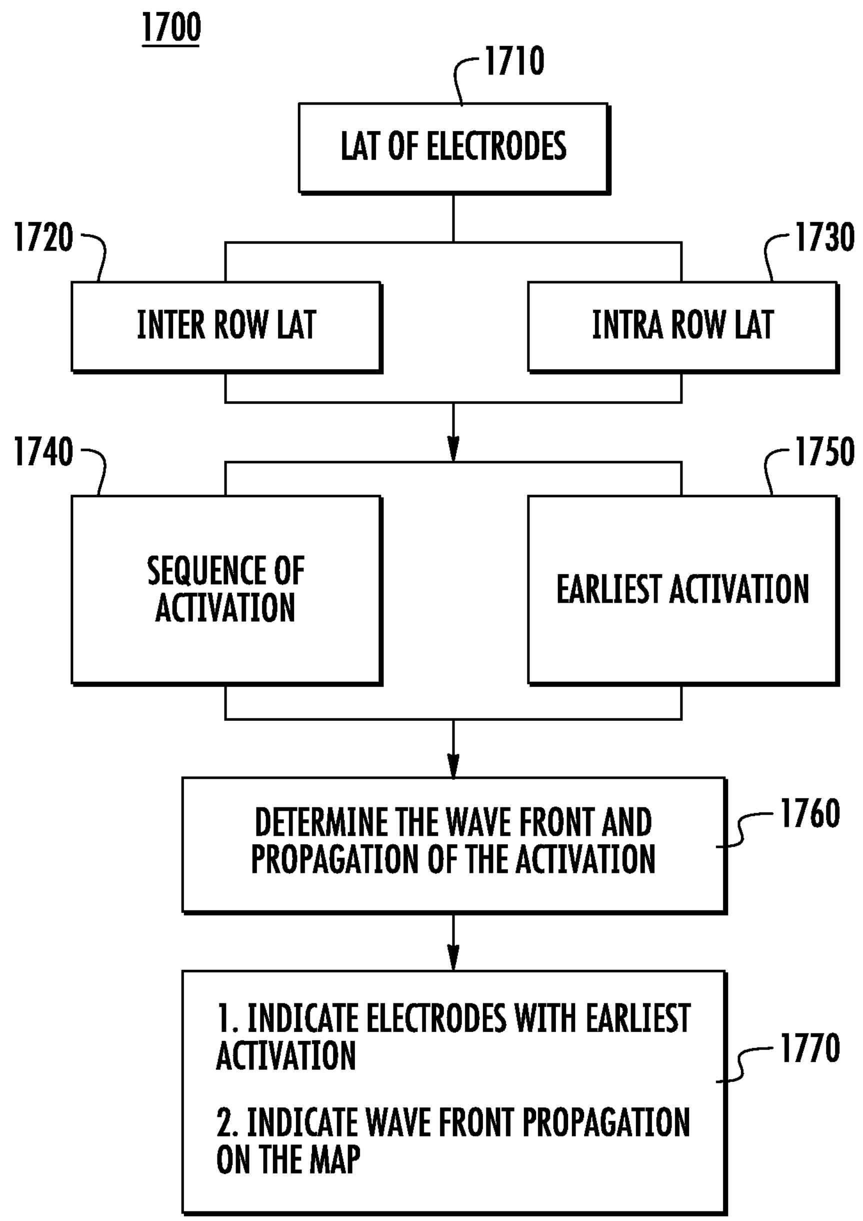
FIG. 17 is a flow diagram of an example method to display an optimal configuration based on a sequence of activation along each row of electrodes.

FIG. 17 is a flow diagram of an example method 1700 to display an optimal configuration based on a sequence of activation along each row of electrodes. This example method 1700 may use the LAT of electrodes 1710 to determine the direction and/or propagation of a wave front and determine the type of activation source. In this example, they system may use the LAT of the electrodes in each row 1720, for example A1-A2, A2-A3, and A3-A4, to determine equivalence in LAT of each electrode in the row and the sequence of activation 1740 along each row of electrodes. The determination of the equivalence of the LATs may be based on a user defined parameter, for example a threshold time of up to 5-10 ms. In parallel, the system may use the LAT of the electrodes on adjacent rows, for example A1-B1, A2-B2, A3-B3, and A4-B4, to determine equivalence in LAT of each electrode in the row and the sequence of activation 1740 between the rows of electrodes.

The system may determine the electrodes with the earliest activation 1750, for example A1, A1/B1 (such as the example in FIG. 10), or A4/B4/C4/D4 (such as the example in FIG. 12). The system may also determine the direction of the propagation 1760, for example A1 to A4, A1/B1 to A4/B4 (such as the example in FIG. 10), or A4/B4/C4/D4 to A1/B1/C1/D1 (such as the example in FIG. 12). The system may then combine the data from the earliest activation 1750 and the data from the direction of the propagation 1760 to determine the wave front of the activation and the propagation of the activation 1770. The system may then indicate and display the catheter electrodes with the earliest activation and the wave front propagation on the anatomical map 1780.

It should be understood that many variations are possible based on the disclosure herein. Although features and elements are described above in particular combinations, each feature or element can be used alone without the other features and elements or in various combinations with or without other features and elements.

The methods provided include implementation in a general purpose computer, a processor, or a processor core. Suitable processors include, by way of example, a general purpose processor, a special purpose processor, a conventional processor, a digital signal processor (DSP), a plurality of microprocessors, one or more microprocessors in association with a DSP core, a controller, a microcontroller, Application Specific Integrated Circuits (ASICs), Field Programmable Gate Arrays (FPGAs) circuits, any other type of integrated circuit (IC), and/or a state machine. Such processors can be manufactured by configuring a manufacturing process using the results of processed hardware description language (HDL) instructions and other intermediary data including netlists (such instructions capable of being stored on a computer readable media). The results of such processing can be maskworks that are then used in a semiconductor manufacturing process to manufacture a processor which implements the methods described herein.

The methods or flow charts provided herein can be implemented in a computer program, software, or firmware incorporated in a non-transitory computer-readable storage medium for execution by a general purpose computer or a processor. Examples of non-transitory computer-readable storage mediums include a ROM, a random access memory (RAM), a register, cache memory, semiconductor memory devices, magnetic media such as internal hard disks and removable disks, magneto-optical media, and optical media such as CD-ROM disks, and digital versatile disks (DVDs).

What is claimed is:

1. A catheter adapted to map a chamber of a heart comprising:

a catheter body configured to form a plurality of non-overlapping concentric loops; and an electrode assembly embedded in the catheter body, wherein the electrode assembly comprises a plurality of electrodes arranged in a plurality of rows, wherein each of the plurality of rows is formed by the plurality of non-overlapping loops, and wherein each of the plurality of rows is configured with a respective plurality of electrodes that are predetermined to be directly aligned with a plurality of electrodes of an opposing row when exiting a sheath; and a processor;

wherein the electrode assembly and the processor are configured to detect a wave front and generate an activation sequence to determine a direction of an activation source, and each concentric loop comprises consists of four electrodes each separated by 90 degrees.

2. The catheter of claim 1, wherein each row of the plurality of rows comprises three electrodes.

3. The catheter of claim 1, wherein each row of the plurality of rows comprises four electrodes.

4. The catheter of claim 1, wherein each row of the plurality of rows comprises five electrodes.

5. The catheter of claim 1, wherein each of the plurality of electrodes in each of the plurality of rows are separated by 3 mm.

6. The catheter of claim 1, wherein the electrode assembly and the processor are configured to determine an activation source type based on the activation sequence.

7. The catheter of claim 6, wherein the activation source type is a focal activation source.

8. The catheter of claim 6, wherein the activation source type is a rotational activation source.

* * * * *

UNITED STATES PATENT AND TRADEMARK OFFICE

CERTIFICATE OF CORRECTION

PATENT NO. : 10,624,554 B2
APPLICATION NO. : 15/404231
DATED : April 21, 2020
INVENTOR(S) : Ziyad Zeidan et al.

It is certified that error appears in the above-identified patent and that said Letters Patent is hereby corrected as shown below:

On the Title Page
In Item (72), under "INVENTORS", in Column 1, Line 1, delete "Zemmer (IL);" and insert -- Zemer (IL); --, therefor.
In Item (72), under "INVENTORS", in Column 1, Line 2, delete "Tivon (IL)" and insert -- Tiv'on (IL) --, therefor.
In Item (57), under "ABSTRACT", in Column 2, Line 12, delete "may be may be" and insert -- may be --, therefor.
In Item (57), under "ABSTRACT", in Column 2, Line 14, delete "and activation" and insert -- an activation --, therefor.

In the Specification
In Column 2, Line 17, delete "(LAT)s" and insert -- (LATs) --, therefor.
In Column 4, Lines 55-56, delete "interest" and insert -- interests --, therefor.
In Column 6, Line 17, delete "focal sources 108" and insert -- focal sources 112 --, therefor.
In Column 6, Line 38, delete "criticality" and insert -- criticality) --, therefor.
In Column 7, Line 37, delete "block 302" and insert -- block 303 --, therefor.
In Column 7, Line 60, delete "median)" and insert -- median)) --, therefor.
In Column 8, Lines 40-41, delete "block 202" and insert -- block 302 --, therefor.
In Column 8, Line 42, delete "block 204" and insert -- block 304 --, therefor.
In Column 8, Line 59, delete "LATs 318," and insert -- LATs, --, therefor.
In Column 18, Line 29, delete "wavefront 1410" and insert -- wave front 1410 --, therefor.
In Column 18, Line 65, delete "wavefront 1410" and insert -- wave front 1410 --, therefor.
In Column 19, Line 36, delete "they" and insert -- the --, therefor.

Signed and Sealed this
Twenty-second Day of November, 2022

Katherine Kelly Vidal

Katherine Kelly Vidal
*Director of the United States Patent and Trademark Office*